(12) United States Patent
Klaiman

(10) Patent No.: US 11,482,320 B2
(45) Date of Patent: Oct. 25, 2022

(54) TRANSFORMATION OF DIGITAL PATHOLOGY IMAGES

(71) Applicant: HOFFMANN-LA ROCHE INC., Little Falls, NJ (US)

(72) Inventor: Eldad Klaiman, Penzberg (DE)

(73) Assignee: HOFFMAN-LA ROCHE INC., Little Falls, NJ (US)

(*) Notice: Subject to any disclaimer, the term of this patent is extended or adjusted under 35 U.S.C. 154(b) by 158 days.

(21) Appl. No.: 16/944,922

(22) Filed: Jul. 31, 2020

(65) Prior Publication Data

US 2021/0005308 A1 Jan. 7, 2021

Related U.S. Application Data

(63) Continuation of application No. PCT/EP2019/053137, filed on Feb. 8, 2019.

(30) Foreign Application Priority Data

Feb. 12, 2018 (EP) ..................................... 18156367

(51) Int. Cl.
*G16H 30/40* (2018.01)
*G06T 7/00* (2017.01)

(52) U.S. Cl.
CPC ........... *G16H 30/40* (2018.01); *G06T 7/0012* (2013.01); *G06T 2207/10064* (2013.01); *G06T 2207/10116* (2013.01); *G06T 2207/20081* (2013.01); *G06T 2207/20084* (2013.01); *G06T 2207/30004* (2013.01); *G06T 2207/30204* (2013.01)

(58) Field of Classification Search
CPC .................. G16H 30/40; G06T 7/0012; G06T 2207/10064; G06T 2207/10116; G06T 2207/20081; G06T 2207/20084; G06T 2207/30004; G06T 2207/30204
See application file for complete search history.

(56) References Cited

U.S. PATENT DOCUMENTS

| 2012/0147002 A1* | 6/2012 | Young .................. G06V 20/695 345/594 |
| 2015/0141278 A1* | 5/2015 | Hollman-Hewgley ..................... G01N 1/30 435/7.1 |

(Continued)

OTHER PUBLICATIONS

International Search Report PCT/ISA/210 for International Application PCT/EP2019/053137, dated Mar. 28, 2019.

(Continued)

*Primary Examiner* — Vu Le
*Assistant Examiner* — Julius Chai
(74) *Attorney, Agent, or Firm* — Harness, Dickey & Pierce, P.L.C.

(57) ABSTRACT

The invention relates to a method of identifying a biomarker in a tissue sample. The method comprises receiving an acquired image depicting a tissue sample, the pixel intensity values of the acquired image correlating with an autofluorescence signal or of an X-ray induced signal or a signal of a non-biomarker specific stain or a signal of a first biomarker specific stain adapted to selectively stain a first biomarker. The acquired image is input into a trained machine learning logic—MLL which automatically transforms the acquired image into an output image highlighting tissue regions predicted to comprise a second biomarker.

13 Claims, 6 Drawing Sheets

(56) References Cited

U.S. PATENT DOCUMENTS

| | | | |
|---|---|---|---|
| 2019/0205760 A1* | 7/2019 | Wiestler | G06T 5/20 |
| 2020/0183327 A1* | 6/2020 | El-Zehiry | G01N 15/1434 |
| 2021/0150701 A1* | 5/2021 | Thagaard | G06T 7/0012 |

OTHER PUBLICATIONS

Written Opinion PCT/ISA/237 for International Application PCT/EP2019/053137, dated Apr. 9, 2019.

Bayramoglu et al., "Towards Virtual H&E Staining of Hyperspectral Lung Histology Images Using Conditional Generative Adversarial Networks", IEEE International Conference on Computer Vision Workshops, 2017.

"Adversarial Stain Transfer for Histopathology Image Analysis", Published In IEEE Transactions on Medical Imaging (vol. 37, issue 3, Mar. 2018).

"Biomarker specific stain", Google Search dated Mar. 8, 2018.

"Biomarker specific stain", Google Search (2) dated Mar. 8, 2018.

International Preliminary Report on Patentability for PCT Application No. PCT/EP2019/053137 dated Aug. 27, 2020.

Isola et al., "Image-to-Image Translation with Conditional Adversarial Networks," Nov. 22, 2017, Berkeley AI Research (BAIR) Laboratory, UC Berkeley.

Kim, et al., "Learning to Discover Cross-Domain Relations with Generative Adversarial Networks," May 15, 2017.

Long et al., "Fully Convolutional Networks for Semantic Segmentation," Mar. 8, 2015.

Goodfellow et al., "Generative Adversarial Nets," Jun. 10, 2014. D'epartement d'informatique et de recherche operationnelle, Universite de Montreal, Montreal, QC H3C 3J7.

Loo Jr. et al., "A new sample preparation method for biological soft X-ray microscopy: nitrogen-based contrast and radiation tolerance properties of glycol methacrylate-embedded and sectioned tissue," Journal of Microscopy, vol. 204, Oct. 2001, pp. 69-86, The Royal Microscopical Society.

Schmahl et al., "Zone Plates for X-Ray Microscopy," X-Ray Microscopy, 1984, Springer-Verlag Berlin Heidelberg.

Niemann et al., "The Gottingen X-Ray Microscopes, " Nuclear Instruments and Methods 208, 1983, pp. 367-371.

Ronneberger et al., "U-Net: Convolutional Networks for Biomedical Image Segmentation," May 18, 2015, Computer Science Department and BIOSS Centre for Biological Signaling Studies, University of Freiburg, Germany.

Zhu et al., "Unpaired Image-to-Image Translation using Cycle-Consistent Adversarial Networks," Aug. 24, 2020.

\* cited by examiner

Acquired H&E stained tissue image

210

Virtual H & FAP & panCK stained tissue image

212

Acquired H&E stained tissue image (zoomed)

214

Virtual H & FAP & panCK stained tissue image (zoomed)

216

— FAP
— panCK

Acquired H & FAP & panCK stained tissue image

218

Acquired H & FAP & panCK stained tissue image (zoomed)

220

— FAP
— panCK

Acquired H & FAP & panCK stained bright field tissue image

TRANSFORMATION OF DIGITAL PATHOLOGY IMAGES

CROSS-REFERENCE TO RELATED APPLICATIONS

This application is a Continuation-In-Part of PCT International Application No. PCT/EP2019/053137, which has an International filing date of Feb. 8, 2019, which further claims priority to European Patent Application No. 18156367.7, filed Feb. 12, 2018, the entire contents of each of which are hereby incorporated by reference.

FIELD OF THE INVENTION

The invention relates to the field of image analysis, and more particular to the field of digital pathology.

BACKGROUND AND RELATED ART

Several image analysis methods are known which can be used to aid the diagnosis process with additional information about the biochemical makeup of cells and other tissue constituents. Generally, computerized histopathology image analysis takes as its input a single- or multi-channel image captured by a camera and attempts to emulate the manual analysis and/or provide additional quantitative information to aid in the diagnosis.

One of the major drawbacks in digital pathology is that typically the tissue needs to be stained in order to reveal relevant biological information, e.g. to reveal cell boundaries, cell types, tissue types or the amount or distribution of certain biomarkers. The staining is an error prone, time consuming and expensive process. The tissue itself is scarce and expensive and so is the time and the materials needed for preparing and staining the tissue sample. Often, limitations in respect to the available tissue and the budget reduce the number of examinations performed on a sample even though it would be beneficial to analyze multiple stainings on each specimen to better understand the disease.

For example, in order to determine the stage of a particular tumor based on an image analysis of a tissue sample image, it may be necessary to stain the sample with a plurality of biomarker-specific stains. Biomarker-specific staining of tissue samples typically involves the use of primary antibodies which selectively bind to the biomarker of interest. In particular these primary antibodies, but also other components of a staining protocol, may be expensive and thus may preclude the use of available image analysis techniques for cost reasons in many application scenarios, in particular high-throughput screenings.

Commonly, tissue samples are stained with a background stain, e.g. a hematoxylin and eosin stain ("H&E" or "HD" stain) in order to reveal the large-scale tissue morphology and the boundaries of cells and nuclei. In addition to the background stain, a plurality of biomarker-specific stains may be applied in dependence on the biomedical question to be answered, e.g. the classification and staging of a tumor, the detection of the amount and relative distribution of certain cell types in a tissue or the like.

SUMMARY

It is an objective of the present invention to provide for an improved method of identifying a biomarker in a tissue sample and a corresponding image analysis system as specified in the independent claims. Embodiments of the invention are given in the dependent claims. Embodiments of the present invention can be freely combined with each other if they are not mutually exclusive.

In one aspect, the invention relates to a method of identifying a biomarker in a tissue sample. The method comprises receiving, by an image analysis system, an acquired image. The acquired image is an image having been acquired by an image acquisition system. The acquired image is one of the following types:

- a digital image of the tissue sample whose pixel intensity values correlate with the strength of an autofluorescence signal or of an X-ray induced signal of the tissue sample; or
- a digital image of the tissue sample whose pixel intensity values correlate with the amount of a non-biomarker specific stain (e.g. hematoxylin, H&E, or the like); or
- a digital image of the tissue sample whose pixel intensity values correlate with the amount of a first biomarker specific stain, the first biomarker-specific stain adapted to selectively stain a first biomarker contained in the tissue sample; or
- a digital image of the tissue sample wherein pixel intensity values of some pixels correlate with the strength of a non-biomarker specific stain (e.g. hematoxylin or H&E or the like) and wherein pixel intensity values of other pixels correlate with the strength of one or more first biomarker specific stains (e.g. Ki67 specific stain).

The method further comprises providing a trained machine learning logic—MLL. The MLL is a machine learning logic having been trained to (explicitly or implicitly) identify tissue regions predicted to comprise a second biomarker. The method further comprises inputting the received acquired image into the MLL and automatically transforming, by the MLL, the acquired image into an output image. The output image highlights tissue regions predicted to comprise the second biomarker. For example, the MLL may be provided as a software product stored on a portable or non-portable data storage device, e.g. a DVD or USB stick or a hard disk drive or may be downloaded via a network, e.g. the Internet or an intranet of a laboratory. Likewise, the MLL may be provided by training an untrained version of the MLL.

Typically, the MLL has been trained on training images depicting tissue samples that have the same or a similar type as the tissue sample depicted in the acquired image. Typically, the tissue samples depicted in the training images have been stained with the same stain and with the same or similar staining protocol like the tissue sample depicted in the acquired image.

The first biomarker in the tissue sample depicted in the acquired image that is selectively stained by the first biomarker-specific stain can also be referred to as "empirical biomarker" or "observed biomarker" because the presence of this biomarker was actually empirically shown by means of the first biomarker-specific stain. The second biomarker is a biomarker that is preferably not stained by the first biomarker-specific stain. The second biomarker can also be referred to as "biomarker of interest" or "MLL-biomarker", because the MLL is a machine learning logic having been trained to predict the presence of this "second biomarker/biomarker of interest/MLL-biomarker based on some training images.

This may be advantageous as the method may generate an output image highlighting the presence of a second biomarker although the acquired image used as input depicts a sample that was not stained at all or was stained by one or more first biomarkers adapted to selectively stain one or more respective first biomarkers, but not the second biomarker. Thus, by providing a MLL that was trained on information that is implicitly contained in an acquired image, explicit information on the presence of a second biomarker in a tissue can be obtained without the need of staining the tissue sample with a stain that is adapted to selectively stain the second biomarker. Thus, valuable time and the costs for the stain for selectively staining the second biomarker can be saved. Applicant has surprisingly observed that the visual information contained e.g. in autofluorescence images, images obtained from an X-ray microscope, images of samples having been stained with a non-biomarker specific stain (e.g. H&E IHC images) as well as images of samples having been stained with one or more stains selectively staining one or more respective first biomarkers (which do not comprise the second biomarker) is sufficient for allowing a MLL having been trained on such images to predict the location of a second biomarker. Without the intention to be bound to any theory, applicant believes that the visual information provided by intrinsic features of the tissue (e.g. features generating a particular autofluorescence signal) or the visual information provided by the unspecific or first biomarker specific stains are sufficient in many cases to generate a reliable implicit or explicit prediction of the presence of a second biomarker even in case the tissue sample has not been stained with a respective second biomarker specific stain. Said visual information may not be sufficient to allow a human to perform this prediction. For example, the presence of a particular biomarker may modify the contrast of cells or organelles, the cell membrane shape or other morphological features of a cell that may not be recognizable by the human eye and/or that may not be interpretable by the human brain, because the interrelations between various visual features and the presence of a particular biomarker may be too complex to be comprehended by a human being. However, applicant has observed that it is possible to train an untrained MLL such that the trained MLL is able to predict the presence of a second biomarker in a tissue based on digital images of said tissue which merely show some tissue intrinsic features like autofluorescence and/or which show the presence and distribution of one or more other (first) biomarkers and/or which show tissue features which can be revealed by non-biomarker specific stains widely used today in the context of immuno histochemistry (IHC).

According to embodiments, the MLL is a machine learning logic having been trained to (explicitly or implicitly) identify tissue regions predicted to comprise a second biomarker in an acquired image.

According to embodiments, the image generated by the image transformation looks like an image generated by the same type of image acquisition system as used for acquiring the input image. For example, the output image generated from an acquired autofluorescence image may look like the original autofluorescence image and in addition comprise highlighted regions being indicative of the second biomarker. The output image generated from an acquired X-ray/bright field microscope/fluorescence image may look like the original X-ray/bright field microscope/fluorescence image and in addition comprise highlighted regions being indicative of the second biomarker.

According to other embodiments, the image generated by the image transformation looks like an image generated by a different type of image acquisition system as used for acquiring the input image. For example, the acquired image can be an image acquired by a fluorescence microscope ("fluorescence image") and the output image can be a virtual H&E image highlighting one or more second biomarkers.

A feature of a tissue sample like "autofluorescence" or "X-ray absorption" or "X-ray transmission" or "X-ray induced fluorescence" may also be referred to as "eigen-property" or "innate characteristic" of the tissue sample.

In some embodiments, the MLL may be trained such that the regions of the tissue sample predicted to comprise the second biomarker are identified explicitly. This means that the coordinates of these regions may be computed by the MLL and they may or may not be provided as output to the user. According to some examples, the output image is basically identical or similar to the acquired image with the only difference that the image regions depicting tissue sample regions predicted to comprise the second biomarker are highlighted. Preferably, the highlighting is performed such that the highlighted tissue regions look like tissue regions having been stained with a conventional biomarker specific stain adapted to selectively stain the second biomarker. All other image regions lacking the second biomarker may basically remain unchanged.

According to some other embodiments, the MLL may be trained such that the regions of the tissue sample predicted to comprise the second biomarker are identified only implicitly. This means that the coordinates of these regions may not be computed by the MLL explicitly and the coordinates are therefore not provided as output to the user. According to some examples, the output image is a virtual staining image that differs from the acquired image in the image regions depicting tissue sample regions predicted to comprise the second biomarker and also in all other regions. For example, the tissue sample regions predicted to comprise the second biomarker can be highlighted and the other image regions may have a different background color and/or contrast than the acquired image. Preferably, the image transformation is performed such that outlook image looks like a typical image of a tissue sample having been stained with a conventional biomarker specific stain adapted to selectively stain the second biomarker. Thus, the MLL may be trained to transform complete acquired images into a respective "virtually stained" output image, whereby all image regions are modified.

For example, the acquired image can be a counter-stained tissue sample image, e.g. a H&E (hematoxylin & eosin) stained tissue sample image or a hematoxylin-stained tissue sample image (counter-staining all nuclei in blue). Then, a MLL having been trained to detect two second biomarkers (Ki67 and CD3) in the counter-stained tissue images is applied on the acquired image and generates a virtual staining image as the output image. The virtual staining image depicts regions in the image predicted to comprise the second biomarker(s), e.g. Ki67 and CD3 biomarkers, and will set the color and intensity values of the respective pixels in the output image such that they look as if they would represent the signal generated by a CD3 or Ki67 specific stain. In addition, the color and intensity values of all other pixels in the image are modified as well, because the output image may represent an image of a tissue sample not having been stained with the H&E stain, but rather having been stained with the CD3 and Ki67 specific stains. Since no eosin stain exists in the output image, the image pixels in the background regions of the output image will not have the typical color of eosin-stained tissue. Thus, the transformation of the acquired image into the output image comprises at least the transformation of the pixels corresponding to the second biomarker but typically/preferably in addition comprises transforming also the other pixels such that the output image looks like an image of a tissue having been stained with a staining protocol adapted to stain the one or more second biomarkers of interest.

According to embodiments, the tissue sample is a sample not having been stained with a stain adapted to selectively stain the second biomarker. Thus, the acquired image is free of any signal generated by a stain that selectively stains the second biomarker.

According to embodiments, the acquired digital image is an image of the tissue sample whose pixel intensity values correlate with the amount of two or more first biomarker specific stains, each first biomarker-specific stain adapted to selectively stain a respective first biomarker contained in the tissue sample, whereby none of the first biomarkers is the second biomarker. In addition, or alternatively, the acquired digital image is an image of the tissue sample whose pixel intensity values correlate with a tissue autofluorescence signal. Still alternatively, the acquired digital image is an image of the tissue sample generated by an X-ray microscope.

According to embodiments, the MLL is a machine learning logic having been trained to (explicitly or implicitly) identify tissue regions predicted to comprise two or more second biomarkers. The output image highlights tissue regions predicted to comprise any of the two or more second biomarkers, whereby preferentially, each of the two or more second biomarkers is highlighted differently, e.g. by simulating stains and their respective color that are typically used or that can be used for selectively staining the two or more second biomarkers.

According to embodiments, the output image is a virtual staining image. The transformation comprises setting the pixel intensity values of the image regions predicted to comprise the second biomarker such that they optically simulate the presence of a second biomarker specific stain. The second biomarker-specific stain is a stain adapted to selectively stain the second biomarker.

According to embodiments, the acquired image is a digital image of the tissue sample whose pixel intensity values correlate with the amount of a first biomarker specific stain. The first biomarker-specific stain is a stain adapted to selectively stain a first biomarker. The first biomarker is selectively contained in a particular cell type. The second biomarker is selectively contained in one out of a plurality of known sub-types of this cell types.

According to one embodiment, the acquired image is a bright field microscope image depicting a tissue sample having been stained with a H&E stain. The output image is a simulated ("virtual") fluorescence image that highlights regions predicted to comprise the biomarker FAP (Fibroblast activation protein alpha) and/or predicted to comprise a cytokeratin visualized via a panCK-antibody-coupled fluorophor. It has been observed that the information contained in an acquired H&E image is sufficient to train an MLL such that the trained MLL is capable of transforming the acquired image into an image correctly highlighting regions comprising FAP and/or cytokeratins.

According to another embodiment, the acquired image is a fluorescence microscope image depicting a tissue sample having been stained with a first fluorescent stain selectively binding to the biomarker Ki67 and with a further first fluorescent stain selectively binding the biomarker CD8. The output image is a simulated ("virtual") fluorescence image that highlights regions predicted to comprise the biomarker FAP and/or predicted to comprise a cytokeratin visualized via a panCK-antibody-coupled fluorophor. It has been observed that the information contained in an acquired image highlighting CD8 and Ki67 is sufficient to train an MLL such that the trained MLL is capable of transforming the acquired image into an image correctly highlighting regions comprising FAP and/or cytokeratins.

This may be advantageous as the method may allow sub-classifying cell types without the necessity to stain the sample with all biomarker specific stains normally considered necessary for performing the sub-classification. For example, H&E stained BF images allow a pathologist to identify T-cells in a tissue, but do not allow a pathologist to identify sub-classes of T cells, e.g. killer cells, helper cells, macrophages, etc. In order to allow for a more fine-granular digital image analysis, the sample must in addition be stained with biomarker specific stains, e.g. stains which selectively bind to biomarkers like CD4, CD3, CD3 and other proteins. Thus, based on state of the art approaches for cell classification in digital pathology, one or more additional staining procedures need to be performed. This implies that additional time and effort is needed for extracting more fine granular information from digital pathology images. To the contrary, applicant has observed that the above mentioned cell types killer cells, helper cells, macrophages can be readily identified by applying a trained MLL on a H&E stained tissue sample image.

According to further embodiments, the second biomarker is a biomarker known to be selectively contained in one of a plurality of known immune cell sub-types. In particular, the second biomarker can be one of: CD4 (i.e., a biomarker whose presence indicates that the cell comprising this biomarker is a T-helper cell) or CD8 (i.e., a biomarker whose presence indicates that the cell comprising this biomarker is a cytotoxic T-cell) or CD3 (a marker for all T-cells) or Foxp3 (i.e., a biomarker whose presence indicates that the cell comprising this biomarker is a regulatory T-cell). The MLL is trained to identify, based on a H&E stained acquired image, tissue regions predicted to comprise any one of the following second biomarkers: CD4, CD8, CD3, Foxp3.

According to still further embodiments, the MLL is trained to identify, based on a H&E stained acquired image, tissue regions predicted to comprise any one of the following second biomarkers: CD4, CD3, and CD8; the output image highlights any of the regions predicted to comprise the CD3, CD4 or CD8 biomarker.

According to another example, the MLL is trained to identify, based on a H&E stained acquired image, tissue regions predicted to comprise the FAP biomarker and tissue regions predicted to comprise one or more tumor specific cytokeratins; the output image highlights the regions predicted to comprise the FAP biomarker (and thus highlights stroma cells which selectively express the FAP protein) and highlights, with one or more different colors, the regions predicted to comprise the cytokines (and thus highlights tumor cells expressing said cytokeratins).

According to embodiments, the acquired image is a digital image of the tissue sample whose pixel intensity values correlate with the amount of a first biomarker specific stain. The first biomarker-specific stain is adapted to selectively stain a first biomarker. The first biomarker is selectively contained in a particular first cell type. The second biomarker is a biomarker known to be selectively contained in one out of a plurality of known sub-types of this first cell type or is a biomarker known to be selectively contained in a second cell type being different from the first cell type.

According to another embodiment, the acquired image is a fluorescence Image of an unstained tissue sample (i.e., an autofluorescence image) and the output image is a virtually generated H&E stained image wherein regions predicted to comprise a biomarker like FAP are highlighted.

According to another embodiment, the acquired image is a multispectral fluorescence image of a tissue sample having been stained with a plurality of specific biomarker stainings, e.g. CD3, CD8, CD4, pan-CK antibody labeled cytokeratines, Ki67 and/or DAPI, and the output image is a virtually generated H&E stained image wherein regions predicted to comprise a biomarker like FAP or cytokeratins ("CK" or "panCK") are highlighted.

According to another embodiment, the acquired image is a multispectral fluorescence image of a tissue sample having been stained with a plurality of specific biomarker stainings, e.g. CD3, CD4, Ki67, FAP, PD1, and/or DAPI and the output image is a virtually generated fluorescence tissue image selectively highlighting CD8 and/or panCK and/or Foxp3 and/or CD168 and/or CD68 and/or blood vessel markers (e.g. CD31).

According to embodiments, the acquired image is a digital image of the tissue sample whose pixel intensity values correlate with the amount of a non-biomarker specific stain. The non-biomarker specific stain is selected from a group comprising: H&E stain, haematoxylin, eosin, Genta, Masson's Trichrome, Gomori Trichrome, Alcian Blue, Ziehl Neelsen stain, Perls' Prussian, Blue Iron, Periodic Acid Schiff (PAS), Modified GMS Silver stain, Carmine, Silver nitrate, Gram Stain, Carcade, Henna, wing fruit extract, China rose extract, sugar beet extract, red rose extract, trichrome stains, Golgi stain, Toluidine Blue, Immunological labeling that have fluorescent or enzymatic stains, Kluver-Barrera stain, Mallory's CT stain and combinations of two or more of said stains.

Said features may be advantageous, because the above mentioned stains are widely used in digital pathology and comparatively cheap. Well established staining protocols and even semi-automated or fully-automated systems for staining tissue samples with some of the above mentioned stains exist for generating a stained tissue sample.

According to embodiments, the acquired image is a digital image of the tissue sample whose pixel intensity values correlate with the amount of a first biomarker specific stain, the first biomarker-specific stain being a fluorescent stain.

For example, the first biomarker specific stain can be any one of Hydroxycoumarin, aminocoumarin, methoxycoumarin, NBD, R-Phycoerythrin (PE), PE-Cy5 conjugates, PE-Cy7 conjugates, Red 613, PerCP, TruRed, FluorX, fluorescein, X-rhodamine, lissamine rhodamine B, an Alexa Fluor dye, a quantum dot, or any other fluorescent stains.

Using an MLL having been trained to identify a second biomarker based on images of a tissue sample having been stained with one or more other, fluorescent based, biomarker specific stains may be advantageous, because a large variety of fluorescent stains with different excitation and emission spectra exist. These florescent stains can often be combined freely with any type of primary antibody for selectively staining certain biomarkers and are therefore widely used in digital pathology. Well established staining protocols and even semi-automated or fully-automated systems for staining tissue samples with some of the above mentioned stains exist for generating a stained tissue sample.

Using a captured image that is generated from a sample having been stained with a non-biomarker specific bright field stain and/or with one or more fluorescent stains may be advantageous as fluorescence and brightfield microscopy imaging of tissue samples and biopsies is widely used in medical diagnosis e.g. for diagnosing of suspected cancer.

Thus, a histological section is likely to be stained one of these techniques and enables a pathologist to identify, with the help of a trained MLL, tumor cells, lymphocytes cells, stroma cells and other types of cells more efficiently without major modifications of the staining protocol (except from that some staining steps may now be obsolete).

Embodiments of the invention can be used in research and development of new drugs and medical techniques. e.g. in drug development, in the localization and quantification of different cells or compartments in the tissue samples in order to understand the drug mode of action and patient response.

According to embodiments, the method further comprises acquiring, by an image acquisition system, the acquired image. The image acquisition system can be, for example, a bright field microscope, a fluorescence microscope or an X-ray microscope. The bright field microscope can be used e.g. for acquiring images of tissue samples stained with one or more bright field stains, e.g. H&E stained samples. A fluorescence microscope can be used in particular for acquiring images of tissue samples having been stained with one or more biomarker-specific stains consisting of e.g. an antibody that is directly or indirectly coupled to a fluorophore, or for generating autofluorescence images, or for generating images of non-biomarker specific fluorescent stains.

The X-ray microscope, in particular a transmission soft X-ray microscope, can also be used for acquiring a digital image of a tissue sample. For example, thin sections of a tissue can be embedded in an embedding medium, e.g. glycol methacrylate polymer, and can be irradiated with X-rays at various radiation doses, typically with doses of up to 10 Gray (see, for example, Loo B W Jr et al., "A new sample preparation method for biological soft X-ray microscopy: nitrogen-based contrast and radiation tolerance properties of glycol methacrylate-embedded and sectioned tissue, 2001 October;204(Pt 1):69-86). X-ray microscopes can achieve higher optical resolution than microscopes using visible light. The wavelength of X-rays is much shorter than the wavelength of visible light, so the limit of the optical resolution (caused by diffraction) of X-ray microscopes is far below the diffraction limit of microscopes working with visible light. The contrast of the images obtained by this technique is primarily based on the nitrogen content of the tissue. The measurements can be calibrated by obtaining the absorption spectrum of protein near the nitrogen edge. The images generated by X-ray microscopes of sections of plastic-embedded soft tissue can be transformed by some trained MLLs into a virtually stained image. According to other embodiments, the acquired X-ray image is an X-ray image in the "water band", i.e. an X-ray image in which the main contrast comes from water molecules (and not nitrogen), see e.g. Pfannkuch F., Hoder D., Baumgärtel H. (1984): "Possible Applications of X-Ray Microscopy in Pathology" in: Schmahl G., Rudolph D. (eds) X-Ray Microscopy. Springer Series in Optical Sciences, vol 43. Springer, Berlin, Heidelberg, Print ISBN 978-3-662-13547-1.

According to still other embodiments, the acquired X-ray image is an X-ray image acquired by a zone plate X-ray microcope (G. Schmahl, D. Rudolph, B. Niemann, O. Christ: X-ray microscopy of biological specimens with a zone plate microscope. Ann. NY. Acad. Sci. 342,368-386 (1980)) or by a scanning x-ray microscopy (B. Niemann, D. Rudolph, G. Schmahl: The Göttingen x-ray microscopes. Nuclear Instruments and Methods 208,367-371 (1983)). X-ray microscopy is currently used e.g. for observing living cells and for observing cell culture monolayers with special regard to their function, such as cell movement, phagocytosis, pinocytosis, cytopempsis, excretion under abnormal conditions (eg., pathological phagocytosis inhibition, lacking excretion of lysosomal enzymes form pathological granulocytes, etc.).

Machine-Learning Approach A ("Supervised Learning")

In the following, a first approach for generating the MLL in a training process is described, that may be referred to as "supervised learning" approach. However, as the distinction of "supervised" and "non-supervised" is sometimes considered to be fluid or gradual, the terms "supervised" and "non-supervised" shall in the following merely imply that the non-supervised approach requires less information in the training data set than the supervised learning approach.

According to embodiments, the method further comprises generating the trained MLL. The generation comprises acquiring, by an image acquisition system, a plurality of first training images. Each first training image depicts a respective training tissue sample and is one of the following types:
- a digital image of a training tissue sample, the pixel intensity values of said digital image correlating with and being indicative of the strength of an autofluorescence or of an X-ray induced signal of the training tissue sample; or
- a digital image of a training tissue sample, the pixel intensity values of said digital image correlating with and being indicative of the strength of a non-biomarker specific stain in the training tissue sample; or
- a digital image of a training tissue sample, the pixel intensity values of said digital image correlating with and being indicative of the strength of amount of a first biomarker specific stain, the first biomarker-specific stain adapted to selectively stain a first biomarker contained in the training tissue sample; or
- a digital image of a training tissue sample wherein pixel intensity values of some pixels correlate with the strength of a non-biomarker specific stain (e.g. H&E or hematoxylin) and wherein pixel intensity values of other pixels correlate with the strength of one or more first biomarker specific stains (e.g. a Ki67 specific stain).

In case the pixel intensities of the first training images are of an image type whose pixel intensities are indicative of the non-biomarker specific stain or of the first biomarker-specific stain, the generation of the MLL can further comprise washing the training tissue samples for removing the non-biomarker specific stain or the first biomarker-specific stain.

The first biomarker in the training tissue sample depicted in a training image can also be referred to as "empirical training biomarker" or "observed training biomarker" because the presence of this biomarker was actually empirically shown by means of the first biomarker-specific stain in the training tissue sample. By training the MLL on the training images, this "empirical training biomarker", the MLL is enabled to predict the presence of this "empirical training biomarker" as the "second biomarker/biomarker of interest/MLL-biomarker" whose presence in a particular input image is predicted by the trained MLL.

The generation of the MLL further comprises staining the training tissue samples with a second biomarker-specific stain. The second biomarker-specific stain is adapted to selectively stain the second biomarker in the training tissue samples. The generation of the MLL further comprises acquiring, by the image acquisition system, a plurality of second training images. Each second training image depicts a respective one of the training tissue samples having been stained with the second biomarker-specific stain. The generation of the MLL further comprises inputting the first and second training images pair wise into an untrained version of the MLL. Each pair of training images depicts the same training tissue sample and is pixel-wise aligned to each other. The generation of the MLL further comprises training the MLL such that the MLL learns to explicitly or implicitly identify regions in the second training images depicting tissue regions in the training tissue samples which are predicted to comprise the second biomarker, whereby the MLL uses intensity information contained in the first training image which depicts the same training tissue sample for the prediction.

Said features may be beneficial, because the pair-wise inputting the first and second training images into the untrained MLL whereby the pixels of the images of each pair is pixel-wise aligned to each other allows to generate and train a MLL that is able to transform any input image having been stained in the same way as the sample in the first digital training image into the image of a sample having been stained like the sample used for generating the second training image. A large body of training information is provided to the MLL during training, because the MLL can learn, for each individual pixel in a first training image how the respective pixel in the "transformed" image has to look like. As the image pairs are aligned pixel-wise, it is not necessary that a human user manually annotates each individual region where the second biomarker is detected in the second training images. Rather, if a respective signal is observed in the second training image, this signal can be considered as a reliable, correct signal, because it is a measured signal having been taken from a camera after having stained the sample with the second biomarker specific stain. Thus, the pair-wise alignment of two images having been acquired empirically from the same sample but after treatment with different staining protocols allows providing an information-rich training data set to the MLL during the training.

In some embodiments, the first training image is an image depicting a sample having been stained with a plurality of biomarker-specific first stains, each first stain being adapted to selectively stain a first biomarker which is different from the second biomarker. The second training image can be an image depicting a training tissue sample having been stained with two or more different second stains respectively being adapted to selectively bind a second biomarker.

According to embodiments, the generation of the training data set may comprise staining the training tissue samples with one or more first stains, acquiring one or more first training images from the samples having been stained with the first stain(s), washing the training samples, staining the training samples with one or more second stains adapted to selectively stain a second biomarker, and acquiring the second training images from the training samples having been stained with the one or more second biomarker specific stains. The first and second training images which depict the same tissue sample are used as image pairs which are fed into the MLL during the training. Preferably, the first and second images are taken under identical or similar conditions regarding e.g. the position of the camera relative to the sample, the resolution, etc. This may ensure that the pixel-wise alignment of the two images will align regions of the images to each other which depict the same regions of the sample. In addition, or alternatively, an automated or manual image registration of the image pairs fed into the MLL is performed to ensure that pixels depicting the same tissue regions are aligned with each other.

Thus, in some example embodiments, the generation of the training data set further comprises staining the training tissue samples with the non-biomarker-specific stain or with the first biomarker specific stain before the first training images are acquired.

According to embodiments, the training of the MLL further comprises training the MLL to learn an image transformation routine. The image transformation routine is adapted to transform each of the first training images into a virtual staining image that is identical or similar to the one of the second training images having been obtained for the same training tissue sample. For example, the image transformation routine may be a routine of transforming an image of a purely H&E stained sample into a virtual staining image in which a particular protein, e.g. FAP, is stained with Alexa Fluor 488. According to another example, the image transformation routine may be a routine of transforming an image of a DAPI stained sample in which in addition the first biomarkers CD3 and CD8 are stained into a virtual staining image wherein only the Foxp3 protein is highlighted in a color corresponding to Alexa Fluor 594. Thus, a large number of different image transformation routines can be easily generated by generating a corresponding training data set and training an untrained MLL on said training data set.

According to embodiments, the MLL is a neural network.

According to embodiments, the neural network is a fully convolutional network, e.g. a network having a U-net architecture.

For example, the network can be a fully convolutional network in which the input is either a FLUORO or a Brightfield image and the output image is an image in which tissue regions predicted to comprise at least one additional biomarker are highlighted.

An example for a suitable fully convolutional network architecture is the "Unet" architecture described by Olaf Ronneberger, Philipp Fischer, and Thomas Brox in "U-Net: Convolutional Networks for Biomedical Image Segmentation", Computer Science Department and BIOSS Centre for Biological Signalling Studies, University of Freiburg, Germany (arXiv:1505.04597v1 18 May 2015). The document can be downloaded via the Cornell University Library https://arxiv.org/abs/1505.04597.

According to embodiments, the neural network is a generative adversarial network, e.g. a network having conditional GAN architecture.

An example for a suitable conditional GAN architecture described by Phillip Isola, Jun-Yan Zhu, Tinghui Zhou, Alexei A. Efros: "Image-to-Image Translation with Conditional Adversarial Networks", Berkeley AI Research (BAIR) Laboratory, UC Berkeley, arXiv:1611.07004v2, 22 Nov. 2017. The document can be downloaded via the Cornell University Library https://phillipi.github.io/pix2pix.%20.

Machine-Learning Approach B ("Non-Supervised Learning")

According to alternative embodiments, the method further comprises generating the trained MLL. The generation of the MLL comprises acquiring, by an image acquisition system, a plurality of first training images. Each first training image depicts a respective training tissue sample and is one of the following types:

a digital image of a training tissue sample, the pixel intensity values of said digital image correlating with and being indicative of the strength of an autofluorescence or of an X-ray induced signal of the training tissue sample; or a digital image of a training tissue sample, the pixel intensity values of said digital image correlating with and being indicative of the strength of a non-biomarker specific stain in the training tissue sample; or a digital image of a training tissue sample, the pixel intensity values of said digital image correlating with and being indicative of the strength of amount of a first biomarker specific stain, the first biomarker-specific stain adapted to selectively stain a first biomarker contained in the training tissue sample;

The generation of the MLL further comprises staining unstained or de-stained versions of the training tissue samples used for acquiring the first training images with a second biomarker-specific stain. In addition, or alternatively, the generation of the MLL comprises staining unstained further training tissue samples with a second biomarker-specific stain. The second biomarker-specific stain is a stain that is adapted to selectively stain the second biomarker in the training tissue samples.

The generation of the MLL further comprises acquiring, by the image acquisition system, a plurality of second training images. Each second training image depicts a respective one of the training tissue samples having been stained with the second biomarker-specific stain.

The generation of the MLL further comprises inputting the first and second training images into an untrained version of the MLL. The first and second training images depicting the same training tissue sample, if any, are neither assigned nor aligned with each other. The generation of the MLL comprises training the MLL such that the MLL learns to explicitly or implicitly identify regions in the second training images which depict tissue regions in the training tissue samples which are predicted to comprise the second biomarker. Thereby, the MLL uses intensity information contained in the first training image which depicts the same training tissue sample for predicting the regions comprising the second biomarker.

Said features may be advantageous, as the first and second training images are not provided in the form of image pairs depicting the same sample to the untrained MLL and the images need not be aligned pixel-wise for being provided as input to the untrained MLL. Thus, the generation of the training data set may require even less manual work than the generation of the training data set for the machine-learning approach "A". Thus, as it is not necessary that the first and the second training images depict the same tissue sample, it is possible that the first and second images depict different tissue samples, e.g. different samples of the same patient, or samples of different patients, etc. This may ease the generation of the training data set. Moreover, it may not be necessary to de-stain already stained samples in order to allow a re-staining with a second biomarker specific stain. Rather, it is possible to simply use other images depicting other samples having been stained with one or more second biomarkers as the second training images. Thus, the time and effort necessary for generating a sufficiently large training data set for generating and training the MLL may be reduced.

According to embodiments, the first training images depict tissue samples having respectively been stained with two or more first stains and/or the second training images depict tissue samples having respectively been stained with two or more second stains as explained already for approach "A".

According to embodiments, the training tissue samples depicted in the first training images are derived from different tissue blocks or different patients than the further training tissue samples depicted in the second training images.

In case the pixel intensities of the first training images are of an image type whose pixel intensities are indicative of the non-biomarker specific stain or of the first biomarker-specific stain, the generation of the training data set may comprise washing the training tissue samples for removing the non-biomarker specific stain or the first biomarker-specific stain. The generation of the training data set may further comprise staining the training tissue samples with the non-biomarker-specific stain or with the first biomarker specific stain before the first training images are acquired. In case the pixel intensities of the first training images are of an image type whose pixel intensities are indicative of the non-biomarker specific stain or of the first biomarker-specific stain, washing the training tissue samples for removing the non-biomarker specific stain or the first biomarker-specific stain. Thus, it is possible to stain, wash, and re-stain the sample as described for the machine-learning approach A. However, the washing steps are optional here, as it would also be possible to use images of other samples having been stained with one or more biomarker specific second stains as the second training images.

According to embodiments, the MLL is a generative adversarial network ("GAN"), in particular a cyclic generative adversarial network ("cyclic GAN") or a DISCO-GAN architecture.

An example for a suitable cyclic GAN network architecture is described by Jun-Yan Zhu, Taesung Park, Phillip Isola, and Alexei A. Efros in "Unpaired Image-to-Image Translation using Cycle-Consistent Adversarial Networks", (24 Nov. 2017). The document can be downloaded via the Cornell University Library https://arxiv.org/abs/1703.10593).

A "DISCO GAN architecture" is an architecture of a generative adversarial network adapted to learn discovering relations between different domains (object types). An example for a suitable DISCO-GAN network architecture is described by Taeksoo Kim, Moonsu Cha, Hyunsoo Kim, Jung Kwon Lee, Jiwon Kim: "Learning to Discover Cross-Domain Relations with Generative Adversarial Networks", arXiv:1703.05192v2, 15 May 2017. The document can be downloaded via the Cornell University Library https://arxiv.org/abs/1703.05192.

According to embodiments, the training of the MLL further comprises training the MLL to learn an image transformation routine. The image transformation routine is adapted to transform each of the first training images into a virtual staining image that is identical or similar to the one of the second training images having been obtained for the same training tissue sample.

According to embodiments, the trained MLL is adapted to perform an image-to-image translation. An image-to-image translation is an image processing operation in which an input image (e.g. one or more first training images) is transformed into an output image (e.g. one or more second training images). The transformation is performed by an MLL having been trained on a training set of aligned or non-aligned images.

In case the training data set does not comprise paired images, the MLL learns to transform an image from a source domain X to a target domain Y in the absence of paired examples. The trained MLL will be adapted to perform non-paired image to image transformation. In the absence of paired images in the training data set, the mapping (or image transformation) G:X→Y is learned such that the distribution of images from G(X) is indistinguishable from the distribution of acquired images Y of the target domain. In other words, during the learning process, the MLL learns to computationally generate ("simulate") output images G(X) such that the difference in the pixel intensity distribution between the simulated images G(X) and the acquired images Y of the target domain is minimized. An image X of the source domain may also be referred to as a "first training image" and an acquired image Y of the target domain may also be referred to as "second training image". Because this mapping is highly under-constrained in the absence of a pair-wise image alignment, embodiments couple the learning of this mapping with the learning of an inverse transformation (or "inverse mapping") F:Y→X and introduce a cycle consistency loss to enforce F(G(X))≈X (and vice versa).

According to some of the embodiments whose MLL comprises a cyclic GAN network architecture, the cyclic GAN comprises four functional units ("blocks"): two "generators" GF, GG and two "discriminators" DF/DG. The generator GG implements and "learns" the image transformation function G adapted for generating output images G(X) mentioned above. The generator GF implements and "learns" the inverse transformation F:Y→X from images of a target domain to images of the source domain. The discriminator DF implements and "learns" to determine whether or not an image was generated by the generator GG or is an acquired, "real" image of the target domain. The discriminator DG implements and "learns" to determine whether or not an image was generated by the inverse generator FG or is an acquired, "real" image of the source domain. All these four blocks participate in the learning process and evaluate and use losses for performing the learning.

The "generators" are optimized for generating "virtual staining images" which are identified by the discriminators as "acquired" image in the respective domain.

For example, if the MLL is trained to transform acquired bright field images of a H&E stained tissue sample as depicted images 202, 204 into images of tissue samples having virtually been stained with hematoxylin (H), Ki67 and CD3 as depicted in images 206, 208, the generator GG learns to generate "virtually stained" images highlighting tissue regions comprising hematoxylin and comprising biomarkers Ki67 and CD3 respectively having been stained with a biomarker specific stain. Acquired H&E images of tissue samples having really been stained with H&E represent images of the source domain. Acquired images of tissue samples having really been stained with H and with Ki67 and CD3 specific stains represent images of the target domain.

In the training, the GF learns to generate images representing the source domain from the acquired images of H & Ki67 and CD3 stained samples. The DF learns to determine whether an image provided by the generator GF is an acquired H&E tissue image or a simulated H&E tissue image. The DG learns to determine whether an image provided by the generator GG is an acquired image of a H & Ki67 and CD3 stained tissue sample or is simulated image depicting a tissue sample having only virtually been stained with H and with Ki67 and CD3 specific stains.

This optimization process can be implemented as a process of minimizing the number of events when the discriminators DG, DF correctly identify an image generated by the generators GG, GF as "fake"/"simulated" rather than "acquired". The learning process may comprise multiple cycles of transforming, by generator GG, an image of the source domain to the target domain and inversely transforming, by generator GF, the image provided by GG into an image of the source domain.

For example, in a first cycle, a source domain image SDI is transformed by GG into an image TDI of the target domain, and TDI is inversely transformed by GF into an image SDI'.

In the second cycle, the source domain image SDI' is transformed by GG into an image TDI' of the target domain, and TDI' is inversely transformed by GF into an image SDI". In the third cycle, the source domain image SDI" is transformed by GG into an image TDI" of the target domain, and TDI" is inversely transformed by GF into an image SDI'". And so on, until a termination criterion is reached.

Upon each image transformation operation of a generator, an adversarial loss is determined, and at the end of each cycle, a cycle loss is determined. The loss of each of the generators GG, GF ("generator loss") consists of the weighted sum of the "adversarial loss" (or "discriminator loss") of the discriminator checking the image generated by the respective generator and the "cyclic loss": Generator_loss=adversarial_loss+w*cycle_loss; where w is an integer. Preferably, w is 10 or a larger integer to indicate the importance of the cycle correctness which implies information in the image is not lost during the transformation. The adversarial loss is the average error the discriminator makes, whereby an error is the classification of a real, acquired image as a fake/simulated image or the classification of a fake image as a real, acquired image. The "adversarial loss" is a measure of the failure of the generator to "fake" (virtually generate/simulate) an image so that the associated discriminator can't accurately predict if this image was empirically acquired in the respective domain or simulated. The "cyclic loss" is a measure of the difference (dissimilarity) of an image generated in one cycle by the generators, e.g. a measure representing the dissimilarity of the images SDI and SDI', or representing the dissimilarity of the images SDI' and SDI", and so on. The training of the MLL comprises minimizing the generator losses of both generators GG, GF.

Using a cyclic GAN based MLL may have the advantage that the MLL can learn to translate between domains without paired input-output examples. It is assumed that there is some underlying relationship between the first training images (or digital pathology images of a first category) and the second training images (or digital pathology images of a second category): for example, there are two different renderings of the same underlying scene—and seek to learn that relationship. Although the training lacks supervision in the form of paired training images, the MLL can exploit supervision at the level of sets: a first set of images in domain X (the first training images, or digital pathology images of a first category) and a different set in domain Y (the second training images, or digital pathology images of a second category). During the training, the MLL learns a mapping G:X→Y such that the output ŷ=G(x), x∈X, is indistinguishable from images y∈Y by an adversary trained to classify ŷ apart from y. In theory, this objective can induce an output distribution over ŷ that matches the empirical distribution $p_{data}(y)$ (in general, this requires G to be stochastic). The optimal G thereby translates the domain X to a domain ŷ distributed identically to Y. However, such a translation does not guarantee that an individual input x and output y are paired up in a meaningful way—there are infinitely many mappings G that will induce the same distribution over ŷ. Moreover, in practice, it has been found it difficult to optimize the adversarial objective in isolation: standard procedures often lead to the well known problem of mode collapse, where all input images map to the same output image and the optimization fails to make progress.

Therefore, the training of the MLL according to embodiments of the invention comprises exploiting the property that translation should be "cycle consistent", in the sense that if a particular input image, e.g. a H&E stained image, is translated into a second image that looks e.g. like an image depicting an hematoxylin stained sample wherein selectively the CD8 biomarker and the Ki67 biomarker are stained with respective biomarker specific stains, and if this second image is then translated back to a "virtual" H&E stained first image, this "virtual" first image is expected to be identical or very similar to the original first image. Mathematically, given a translator G:X→Y and another translator F:Y→X, then G and F should be inverses of each other, and both mappings should be bijections. This structural assumption is applied by training both the mapping G and F simultaneously during the training of the MLL, and adding a cycle consistency loss that encourages F(G(x))≈x and G(F(y))≈y. Combining this loss with adversarial losses on domains X and Y yields our full objective for unpaired image-to-image translation.

In a further aspect, the invention relates to an image analysis system comprising one or more processors and a volatile or non-volatile storage medium. The storage medium comprises an acquired image. The acquired image is an image having been acquired by an image acquisition system. The acquired image is one of the following types:

a digital image of the tissue sample whose pixel intensity values correlate with the strength of an autofluorescence signal or of an X-ray induced signal of the tissue sample; or a digital image of the tissue sample whose pixel intensity values correlate with the amount of a non-biomarker specific stain; or a digital image of the tissue sample whose pixel intensity values correlate with the amount of a first biomarker specific stain, the first biomarker-specific stain adapted to selectively stain a first biomarker contained in the tissue sample.

The storage medium further comprises a trained machine learning logic (MLL) MLL, wherein the MLL has been trained to explicitly or implicitly identify tissue regions predicted to comprise a second biomarker. According to preferred embodiments, the MLL has been trained to explicitly or implicitly identify tissue regions predicted to comprise a second biomarker in an acquired image(s) of the same type as the received acquired image (e.g. autofluorescence images, images with an X-ray induced signal, images with signals of a non-biomarker-specific stain or images with signals of one or more first-biomarker specific stain respectively being indicative of a particular first biomarker, whereby none of the first biomarkers is the second biomarker).

The storage medium further comprises a program logic executable by the one or more processors and being configured to inputting the received acquired image into the MLL.

The MLL is configured to automatically transform the acquired image into an output image. The output image highlights tissue regions predicted to comprise the second biomarker.

In a further aspect, the invention relates to an image-to-image translation method. The method comprises receiving, by an image analysis system, a digital pathology image of a first category; and automatically transforming, by a trained machine learning logic (MLL) being a trained GAN network, the digital pathology image of the first category into a digital pathology image of a second category. The GAN network is a cyclic generative adversarial network or a network having conditional GAN architecture or a network having DISCO-GAN architecture.

According to embodiments of the image-to-image translation method, the digital pathology image of the first category is an acquired image highlighting first regions of a tissue sample, wherein the first regions are auto-fluorescent regions, regions emitting X-ray or X-ray induced signals, regions stained with a non-biomarker specific first stain or regions comprising one or more specifically stained first biomarkers. The digital pathology image of the second category is a virtual staining image. The virtual staining image highlights second regions of the tissue sample, wherein the second regions are regions of the tissue sample predicted by to comprise a second biomarker.

According to some embodiments, the virtual staining image highlights the regions of the tissue sample predicted by to comprise a second biomarker and in addition highlights regions of the tissue having been predicted to comprise a particular type of molecule, e.g. nucleic acids, lipids, proteins, or acidic molecules or basic molecules, thereby simulating some generic stains such as hematoxylin selectively binding to nuclei or eosin selectively binding to eosinophilic structures such as intracellular proteins, mitochondria, smooth endoplasmic reticulum, collagen, keratin and the like.

According to still other embodiments, the virtual staining image does not highlight second regions of the tissue sample predicted by to comprise a second biomarker, but rather highlights regions of the tissue having been predicted to comprise a particular type of molecule. A "tissue sample" as used herein is a 3D assembly of cells that may be analyzed by the methods of the present invention. The 3D assembly can be an assembly of an ex-vivo cell block, e.g. a tissue sample, or an in-vivo specimen (in particular in the case of X-ray images or X-ray induced images). For example, the sample may be prepared from tissues collected from patients, animals, fungi or plants. Alternatively, the sample may be a cell containing biological sample such as a bone marrow sample, or a cell line or a cell block manufactured from a plurality of cells. The samples may be whole-tissue or TMA sections on microscope slides. Particularly when using tissue microarrays (TMAs), samples may be arranged as "spots" or "histospots" on a slide, with each histospot corresponding to a particular sample. Such methods for preparing slide mounted tissue samples are well known in the art and suitable for use in the present invention.

Tissue samples may be stained using any reagent or biomarker label, such as dyes or stains, histochemicals, or immunohistochemicals that directly react with the specific biomarkers or with various types of cells or cellular compartments. Not all stains/reagents are compatible. Therefore the type of stains employed and their sequence of application should be well considered, but can be readily determined by one of skill in the art. Such histochemicals may be chromophores detectable by transmittance microscopy or fluorophores detectable by fluorescence microscopy. In general, cell containing samples may be incubated with a solution comprising at least one histochemical, which will directly react with or bind to chemical groups of the target. Some histochemicals must be co-incubated with a mordant or metal to allow staining. A cell containing sample may be incubated with a mixture of at least one histochemical that stains a component of interest and another histochemical that acts as a counterstain and binds a region outside the component of interest. Alternatively, mixtures of multiple probes may be used in the staining, and provide a way to identify the positions of specific probes. Procedures for staining cell containing samples are well known in the art. Examples for X-ray microscopy compatible stains include enzyme peroxidases (such as HRP or APEX), photo-sensitiser proteins (such as miniSOG), and photosensitive dyes that associate with proteins, or short peptides, such as ReASH.

An "image analysis system" as used herein is a system, e.g. a computer system, adapted to evaluate and process digital images, in particular images of tissue samples, in order to assist a user in evaluating or interpreting an image and/or in order to extract biomedical information that is implicitly contained in the image. For example, the computer system can be a standard desktop computer system or a distributed computer system, e.g. a cloud system.

The expression "explicitly identifying a tissue region predicted to comprise the second biomarker" as used herein means that the algorithm performing the identification determines the positions of the pixels in the image having been predicted to comprise the second biomarker and thus is able to output or actually outputs the positions of the identified regions in the form of coordinates. To the contrary, an "implicit identification" means that the algorithm performing the transformation may selectively modify the pixels in the identified region differently from the pixels in the different regions, but is not able to output the coordinates of said regions in the image. It is merely able to modify some or all pixels in the acquired image such that an output image is generated wherein some regions are highlighted, and the highlighted regions represent regions predicted to comprise the second biomarker.

An "X-ray microscope" is a microscope adapted to use electromagnetic radiation in the soft X-ray band to produce magnified images of objects. Since X-rays penetrate most objects, there is no need to specially prepare them for X-ray microscopy observations. Unlike visible light, X-rays do not reflect or refract easily, and they are invisible to the human eye. Therefore, an X-ray microscope exposes film or uses a charge-coupled-device (CCD) detector to detect X-rays that pass through the specimen. It is a contrast imaging technology using the difference in absorption of soft X-rays in the water window region (wavelengths: 2.34-4.4 nm, energies: 280-530 eV) by the carbon atom (main element composing the living cell) and the oxygen atom (main element for water).

The term "digital pathology" as used herein is an IT-environment designed for information management of data generated from a digital slide. Accordingly, a "digital pathology image" is a digital image, typically an image depicting a tissue sample, that is generated, analyzed and/or modified within a digital pathology IT environment. Thus, the term "digital pathology" should be interpreted broadly. It is not limited to the diagnosis and treatment of a disease, but may rather also encompass digital images of tissue samples drawn from healthy organisms, e.g. for the purpose of research. With the advent of whole-slide Imaging, the field of digital pathology has exploded and is currently regarded as one of the most promising avenues of diagnostic medicine in order to achieve even better, faster and cheaper diagnosis, prognosis and prediction of cancer and other important diseases. Digital pathology is also widely used in drug research and development as it may help revealing a drug's mode of action and the effect seen in the tumor's microenvironment. A digital image acquired by an image acquisition system or generated virtually by computational means can be, for example, a single channel image or a multichannel image. In some embodiments, the digital image is an rgb image.

A "virtual staining image" or a "virtually stained image" as used herein is a digital image that looks like an image that depicts a tissue sample, e.g. a tissue sample having been stained in accordance with a particular staining protocol, but that has not been acquired by an image acquisition system. Rather, a "virtually stained image" has been computationally generated from scratch or based on an acquired tissue sample image.

A "training tissue sample" as used herein is a tissue sample from which one or more training images are acquired, whereby the training images are used for providing the training data set used for training the MLL. Depending on the particularities of the case, the MLL is trained some hours, days, weeks or even month before the trained MLL is used for transforming acquired images into output images. Accordingly, the training tissue sample is often, but not necessarily, derived from another source, e.g. from another organism of the same species, as the tissue sample depicted in the acquired image.

A "training image" as used herein is an image acquired from a training tissue sample. The training images are used for training an untrained version of the MLL for generating a trained MLL that is adapted to transform an acquired tissue image into an output image that highlights a specific biomarker although the tissue sample was not stained with a stain suited for selectively staining said biomarker.

A "virtual staining image" is an image that is not captured by an image acquisition system, but is rather generated computationally de novo or by transforming an acquired image of a tissue sample into a new image. The new image looks like an image of a tissue sample having been stained according to a particular protocol although the tissue sample depicted in the acquired image from which the virtual staining image is derived, if any, was not stained in accordance with said protocol. Thus, the pixel intensity and color values "simulate" the effect of said particular staining protocol.

An image "highlighting" tissue regions predicted to comprise the second biomarker as used herein means that the intensity values and/or the color of the pixels within said regions are set such that said regions are the brightest or darkest regions within the image or are regions having a particular color. Preferably, the pixel intensity and/or color values in said regions and in the other image regions predicted not to comprise the second biomarker are set such that the output image looks like an image of a real tissue sample having been stained with one or more known second stains according to known tissue staining protocols, each second stain being adapted to selectively stain a respective one of the one or more biomarkers. As the word "staining" implies, the color and intensity values generated by a "real" second stain will be suitable for attracting the attention of a human, because regions stained with a second stain will be significantly darker or significantly brighter or will have a significantly different color than other tissue regions not comprising the second biomarker. Thus, the second stain is adapted to stain and "highlight" tissue regions comprising a particular second biomarker, and the MLL is trained to generate an output image that comprises a simulated staining effect of a second stain in regions of the image depicting tissue sample regions predicted to comprise the second biomarker. This simulated staining effect of a second stain in the output image is referred herein "highlighting" of regions of the output image.

The term "intensity information" or "pixel intensity" as used herein is a measure of the amount of electromagnetic radiation ("light") captured on or represented by a pixel of a digital image. The term "intensity information" as used herein may comprise additional, related information, e.g. the intensity of a particular color channel. A MLL may use this information for computationally extracting derivative information such as gradients or textures contained in a digital image, and the derivative information may be implicitly or explicitly extracted from the digital image during training and/or during an image transformation of the trained MLL. For example, the expression "the pixel intensity values of a digital image correlate with the strength of one or more particular stains" can imply that the intensity information, including color information, allows the MLL and may also allow a user to identify regions in tissue sample having been stained with a particular one of said two or more stains. For example, pixels depicting a region of a sample stained with hematoxylin may have high pixel intensities in the blue channel, pixels depicting a region of a sample stained with fastRed may have high pixel intensities in the red channel.

A "generative adversarial network" (GAN) as used herein is a type of neural network architecture used in machine learning, in particular in unsupervised machine learning. A GAN is a system of two neural networks contesting with each other in a zero-sum game framework. GANs were introduced by Ian Goodfellow et al. in 2014 (Goodfellow, Ian; Pouget-Abadie, Jean; Mirza, Mehdi; Xu, Bing; Warde-Farley, David; Ozair, Sherjil; Courville, Aaron; Bengio, Joshua: "Generative Adversarial Networks"a. rXiv: 1406.2661 https://arxiv.org/abs/1406.2661). Embodiments of the invention use an MLL of the GAN type for computationally generating a virtually stained output image from an acquired image, whereby the virtual staining image typically looks authentic to human observers.

A "cyclic-GAN" as used herein is a GAN that fulfills Cycle Consistency. Cycle consistency is a criterion that requires than a transformation of input data to output data based on a first transformation logic can be reversed by a backward transformation logic adapted to transform the output data back into the input data such that the input data generated by the back-transformation is basically identical to or very similar to the original input data. The input data may be image data. A cyclic GAN requires forward-backward consistency and uses cycle consistency loss as a way of using transitivity to supervise the training of the neural networks contained in a cyclic GAN. A MLL implemented as a cyclic GAN is adapted to learn to transform an input image into an output image even in the absence of a clear pairing of input and output training images. It is sufficient that training images of two different categories, i.e., a set of input images and a set of output images, is provided to the untrained MLL. During the training, the cyclic GAN learns to transform an image from a source domain X to a target domain Y in the absence of paired examples as explained already above. The trained MLL will be adapted to perform non-paired image to image transformation. In the absence of paired images in the training data set, the mapping $G:X \to Y$ is learned such that the distribution of images from $G(X)$ is indistinguishable from the distribution Y using an adversarial loss. An image X of the source domain may also be referred to as a "first training image" and the image Y of the target domain may also be referred to as "second training image". Because this mapping is highly under-constrained in the absence of a pair-wise image alignment, a cyclic GAN couples the learning of this mapping with the learning of an inverse mapping F:Y→X and introduce a cycle consistency loss to enforce F(G(X))≈X (and vice versa). During the training, the MLL learns a mapping G:X→Y such that the output ŷ=G(x), x∈X, is indistinguishable from images y∈Y by an adversary trained to classify ŷ apart from y. Thus, the training of the MLL according to embodiments of the invention comprises exploiting the property that translation should be "cycle consistent".

A "fully convolutional neural network" as used herein is a neural network composed of convolutional layers without any fully-connected layers or multilayer perceptron (MLP) usually found at the end of the network. A fully convolutional net is learning filters in every layer. Even the decision-making layers at the end of the network learn filters. A fully convolutional net tries to learn representations and make decisions based on local spatial input.

According to embodiments, the fully convolutional network is a convolutional networks with only layers of the form whose activation functions generate an output data vector $y_{ij}$ at a location (I, j) in a particular layer that satisfies the following properties:

$$y_{ij}=f_{ks}(\{x_{si+\delta i,sj+\delta j}\}_{0\leq \delta i,\delta j\leq k})$$

Wherein $x_{ij}$ is a data vector at location (i; j) in a particular layer, and $y_{ij}$ is the data vector at said location in the following layer, wherein $y_{ij}$ is an output generated by the activation functions of the network, where k is called the kernel size, s is the stride or subsampling factor, and $f_{ks}$ determines the layer type: a matrix multiplication for convolution or average pooling, a spatial max for max pooling, or an elementwise nonlinearity for an activation function, and so on for other types of layers. This functional form is maintained under composition, with kernel size and stride obeying the transformation rule:

$$f_{ks} \circ g_{k's'} = (f \circ g)_{k'+(k-1)s', ss'}.$$

While a general deep net computes a general nonlinear function, a net with only layers of this form computes a nonlinear filter, which we call a deep filter or fully convolutional network. An FCN naturally operates on an input of any size, and produces an output of corresponding (possibly resampled) spatial dimensions. For a more detailed description of the characteristics of several fully convolutional networks see Jonathan Long, Evan Shelhamer, and Trevor Darrell: "Fully Convolutional Networks for Semantic Segmentation", CVPR 2015.

A "machine learning logic (MLL)" as used herein is a program logic, e.g. a piece of software like a trained neuronal network or a support vector machine or the like that has been trained in a training process and has learned during the training process to perform some predictive and/or data processing tasks based on the provided training data. Thus, an MLL can be a program code that is at least partially not explicitly specified by a programmer, but that is implicitly learned and modified in a data-driven learning process that builds one or more implicit or explicit models from sample inputs. Machine learning may employ supervised or unsupervised learning. Effective machine learning is often difficult because finding patterns is hard and often not enough training data are available.

The term "biomarker" as used herein is a molecule that may be measured in a biological sample as an indicator of tissue type, normal or pathogenic processes or a response to a therapeutic intervention. In a particular embodiment, the biomarker is selected from the group consisting of: a protein, a peptide, a nucleic acid, a lipid and a carbohydrate. More particularly, the biomarker may be a protein. Certain markers are characteristic of particular cells, while other markers have been identified as being associated with a particular disease or condition.

Examples of known prognostic markers that can be used as first or second biomarkers according to embodiments of the invention include enzymatic markers such as, for example, galactosyl transferase II, neuron specific enolase, proton ATPase-2, and acid phosphatase. Hormone or hormone receptor markers include human chorionic gonadotropin (HCG), adrenocorticotropic hormone, carcinoembryonic antigen (CEA), prostate-specific antigen (PSA), estrogen receptor, progesterone receptor, androgen receptor, gC1q-R/p33 complement receptor, IL-2 receptor, p75 neurotrophin receptor, PTH receptor, thyroid hormone receptor, and insulin receptor. Other biomarkers may include the FAP protein or a cluster of differentiation (CD) marker, e.g. D1a, CD1b, CD1c, CD1d, CD1e, CD2, CD3delta, CD3epsilon, CD3gamma, CD4, CD5, CD6, CD7, CD8alpha, CD8beta, CD9, CD10, CD11a, CD11b, CD11c, CDw12, CD13, CD14, CD15, CD15s, CD16a, CD16b, and others. Other biomarkers may include lymphoid markers, e.g. alpha-1-antichymotrypsin, alpha-1-antitrypsin, B cell marker, bcl-2, bcl-6, B lymphocyte antigen 36 kD, BM1 (myeloid marker), BM2 (myeloid marker), galectin-3, granzyme B, HLA class I Antigen, HLA class II (DP) antigen, HLA class II (DQ) antigen, HLA class II (DR) antigen, human neutrophil defensins, immunoglobulin A, immunoglobulin D, immunoglobulin G, immunoglobulin M, kappa light chain, and others. Other biomarkers may include tumor markers, e.g. alpha fetoprotein, apolipoprotein D, BAG-1 (RAP46 protein), CA19-9 (sialyl lewisa), CA50 (carcinoma associated mucin antigen), CA125 (ovarian cancer antigen), CA242 (tumour associated mucin antigen), chromogranin A, clusterin (apolipoprotein J), epithelial membrane antigen, epithelial-related antigen, epithelial specific antigen, epidermal growth factor receptor, estrogen receptor (ER), gross cystic disease fluid protein-15, hepatocyte specific antigen, HER2, heregulin, human gastric mucin, human milk fat globule, MAGE-1, matrix metalloproteinases, tyrosinase, tyrosinase-related protein-1, villin, von Willebrand factor, CD34, CD34, Class II, CD51 Ab-1, CD63, CD69, Chk1, Chk2, claspin C-met, COX6C, CREB, Cyclin D1, Cytokeratin, Cytokeratin 8, DAPI, Desmin, DHP (1-6 Diphenyl-1,3,5-Hexatriene), and others.

Other biomarkers may include cell cycle associated markers, e.g. apoptosis protease activating factor-1, bcl-w, bcl-x, bromodeoxyuridine, CAK (cdk-activating kinase), cellular apoptosis susceptibility protein (CAS), caspase 2, and others. Other biomarkers may include neural tissue and tumor markers, e.g. alpha B crystallin, alpha-internexin, alpha synuclein, amyloid precursor protein, beta amyloid, calbindin, choline acetyltransferase, excitatory amino acid transporter 1, GAP43, glial fibrillary acidic protein, glutamate receptor 2, myelin basic protein, nerve growth factor receptor (gp75), neuroblastoma marker, and others. Other cellular markers include centromere protein-F (CENP-F), giantin, involucrin, lamin A&C [XB 10], LAP-70, mucin, nuclear pore complex proteins, p180 lamellar body protein, ran, r, cathepsin D, Ps2 protein, Her2-neu, P53, S100, epithelial marker antigen (EMA), TdT, MB2, MB3, PCNA, and Ki67.

According to embodiments of the invention, a "biomarker specific stain" is a stain that has a specific affinity for particular biomarker. For example, the biomarker specific stain can be a stain commonly used in histology and microchemistry for identifying a particular biomarker, e.g. by coupling the stain to a specific detection system such as an antibody. To the contrary, a "non-biomarker specific stain" can be, for example, a stain that has specific affinity for substances having a particular physical or chemical parameter in a particular range, e.g. having a particular polarity or pH value. For example, eosin is an acidic dye: it is negatively charged and stains basic (or acidophilic) structures red or pink.

BRIEF DESCRIPTION OF THE DRAWINGS

In the following embodiments of the invention are explained in greater detail, by way of example only, making reference to the drawings in which:

FIG. 1 depicts a flowchart of a method 100 of identifying a biomarker in a tissue sample according to an embodiment of the invention. The biomarker of interest is in the following also referred to as "second biomarker". For the sake of simplicity, most embodiments described herein mentioned only a single second biomarker, but the invention can likewise be used for generating and using a MLL that is adapted to identify regions in a tissue sample comprising two or more different biomarkers of interest.

Figure 3:
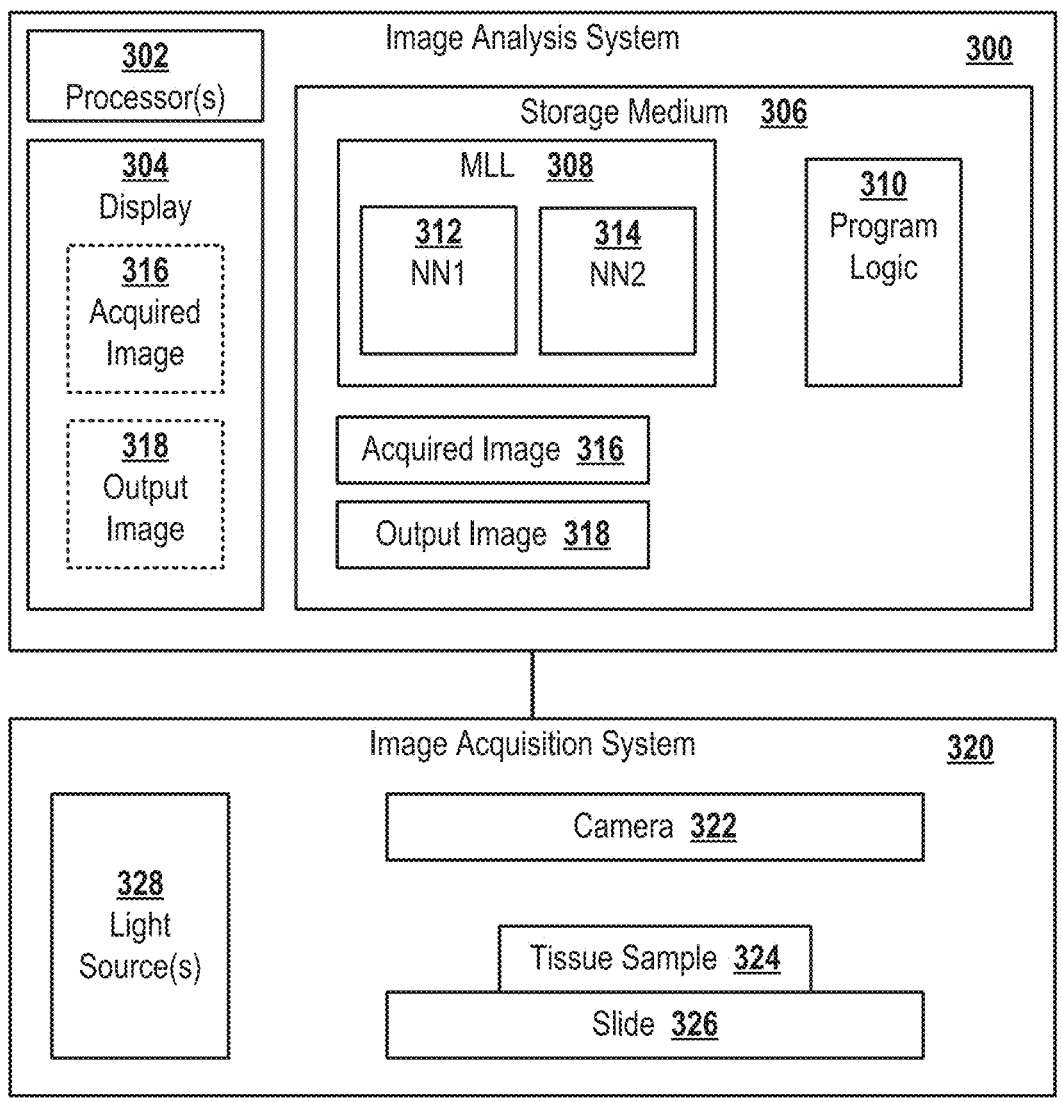
FIG. 3 depicts a block diagram of an image analysis system according to an embodiment of the invention.

In a first step 102, in the image analysis system receives an acquired image of a tissue sample. For example, the image analysis system can be a system 300 as depicted in FIG. 3. In the following, reference will also be made to elements of FIG. 3.

The tissue sample 324 can be a tissue sample from any tissue and any organism. In particular, the tissue sample can be a thin tissue slice derived from a biopsy from a human or non-human animal; it can be a slice of a paraffin embedded cell block or the like. The image can be received via a network interface, e.g. via the Internet or an intranet from a cloud storage server or any other source. The images can also be read from a one storage medium or can directly be received from an image acquisition system 320 that can optionally be coupled to the image analysis system 300.

The tissue sample depicted in the received acquired image can be, for example, a digital image of the tissue sample whose pixel intensity values correlate with the strength of an autofluorescence signal or of an X-ray induced signal of the tissue sample. In this case, the tissue sample can be a completely un-stained sample or can be stained by a non-biomarker-specific stain. It is also possible that the tissue sample depicted in the received acquired image is stained with one or more first biomarker specific stains which selectively staining first biomarkers, but not the second biomarker whose presence and localization shall be determined not empirically, but computationally ("virtually staining"). Irrespective of whether or not the tissue sample depicted in the acquired image is stained or not, the image was acquired under conditions under which the tissue's autofluorescence signal was the most prominent signal captured by the image acquisition system. Thus, it is possible that the acquired image shows a mixture of autofluorescence signal and some staining signals, but is hereby assumed that the most prominent signal is derived from autofluorescence. Autofluorescence images of tissue samples are examples of images captured by a fluorescent microscope. However, an autofluorescence image is not the only possible type of acquired image that can be used for embodiments of the invention.

For example, the received acquired image can be an image of an X-ray microscope and the pixel intensities in the acquired image may correspond to signals directly or indirectly induced by the X-rays. For example, depending on the particular type of X-ray microscope used, the signal is captured by the acquired image may correspond to a scattered or transmitted X-rays or may correspond to fluorescent signals having been induced by the X-rays interacting with molecules in the sample. Again, the tissue sample can be an un-stained sample or a sample having being stained by one or more stains (but not with a biomarker-specific stain adapted to bind to the second biomarker of interest).

Still alternatively, the tissue sample depicted in the acquired image can be a digital image of the tissue sample whose pixel intensity values correlate with the amount of a non-biomarker specific stain, e.g. H&E stain, Giemsa stain, or the like.

Still alternatively, the tissue sample depicted in the acquired image can be a tissue sample having being stained with one or more first biomarker specific stains. For example, the tissue sample may have been stained with the first fluorescent probe selectively binding to the CD3 biomarker and with the first fluorescent probe selectively binding to the CD8 biomarker. Optionally, the tissue sample may have been stained with a background stain like H&E. However, if it is the task of the methods to ritually simulate the staining of the biomarker Foxp3, the tissue sample has not been stained with any stain being adapted to selectively bind to the biomarker of interest, here: Foxp3.

Next in step 104, the method comprises providing a trained machine learning logic—MLL 308. The MLL can be, for example, a neural network having been trained on a plurality of training images to identify tissue regions predicted to comprise a second biomarker, e.g. Foxp3.

Next in step 106, the received acquired image is input to the MLL. Although many different types of acquired images can be used in various embodiments of the invention, it is important that the type of acquired image used is identical or very similar to the type of images used during the training phase of the MLL. For example, if the acquired image is an autofluorescence image, the MLL is required to have been trained also on autofluorescence images of tissue samples rather than X-ray images. And if the received acquired image depicts a tissue sample having been stained with three marker specific first stains A, B and C, the MLL is required to have been trained also on images of tissue samples having been stained with marker specific first stains A, B C rather than D or E.

Next in step 108, the MLL automatically transforms the acquired image into an output image. The output image highlights tissue regions predicted to comprise the second biomarker. The output image can be displayed to a user on a display 304, e.g. an LCD display, or can be print out all provided by any other means to a user for further analysis.

Figure 1:
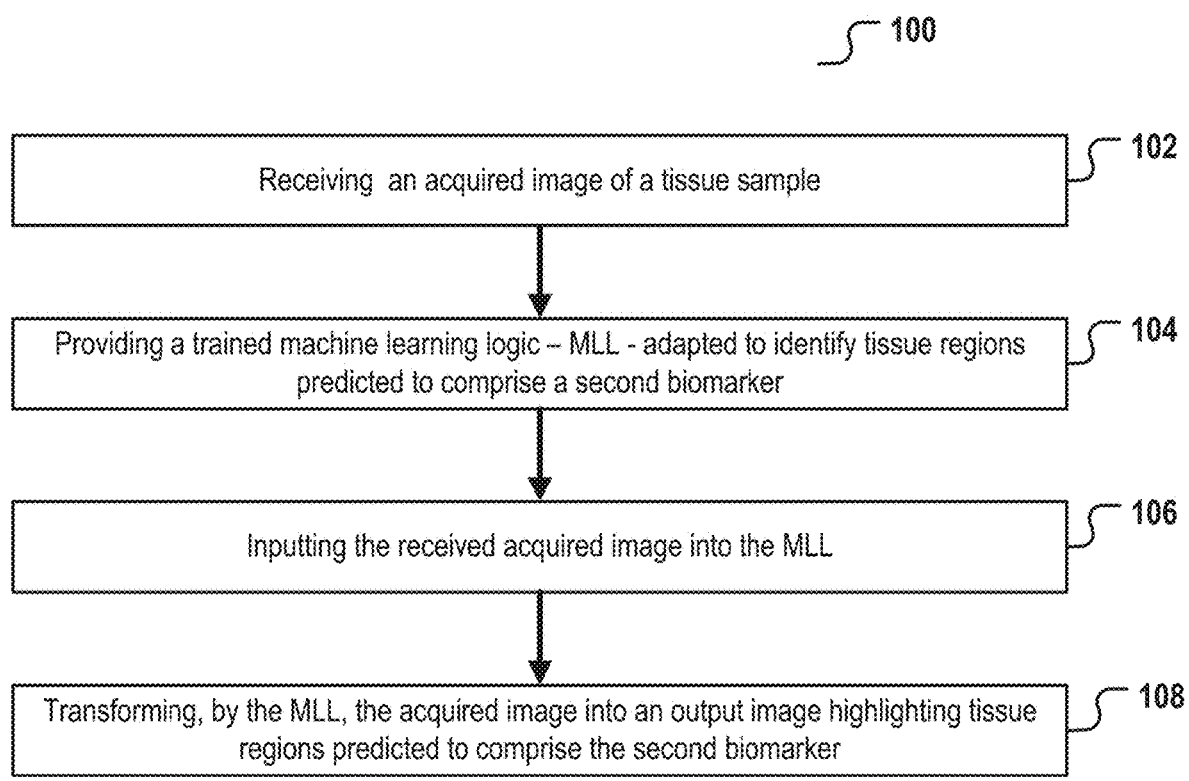
FIG. 1 depicts a flowchart of a method according to an embodiment of the invention.
Figure 2A:
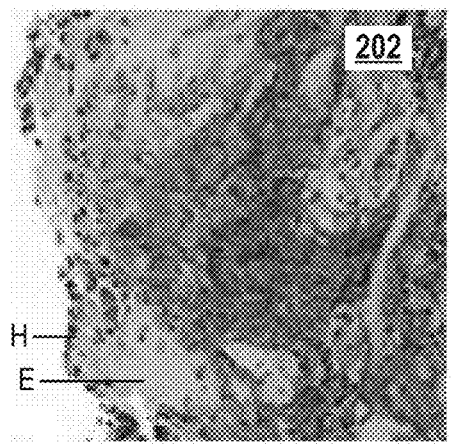
FIGS. 2A-2G depicts multiple pairs of acquired input images and virtual staining image generated therefrom.
Figure 2A:
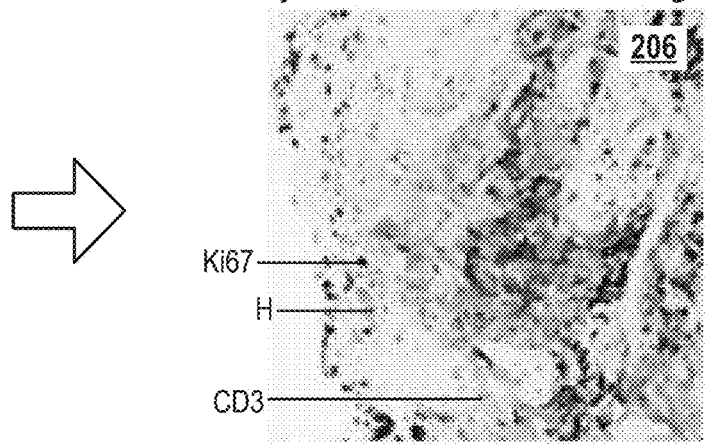

FIG. 2A depicts an acquired bright field microscope input image 202 that depicts a human liver tissue sample having been stained with H&E stain and depicts a corresponding output image 206 having been generated from the acquired image by the MLL in an image transformation operation.

In an H&E stained tissue sample image, the nuclei are stained in blue/purple, the basophils in purplish red, the cytoplasm in red, muscle cells, if any, in dark red, erythrocytes, if any, in cherry red, collagen and mitochondria in pale pink.

The output image 206 is a virtual staining image that looks identical or confusingly similar to a bright field image of a tissue sample having been stained with hematoxylin (H), with a Ki67 specific brown stain comprising DAB and with a CD3 specific red stain comprising fastRed. As can be inferred by a comparison of images 202 and 206, different regions are highlighted (by particularly dark color) in the virtual staining image than in the acquired image. This is because in the virtual staining image, tissue regions predicted to comprise the second biomarker Ki67 are highlighted in brown, and tissue regions predicted to comprise the second biomarker CD3 are highlighted in red. However, not only the biomarker specific regions of the image have changed their intensity during image transformation: also the pixel intensities of the background pixels corresponding to tissue regions not predicted to comprise the second biomarker have changed during the transformation and have become significantly brighter in the output image 206 than in the acquired image 202. Thus, although the input image as well as the output image highlights real or predicted hematoxylin-containing nuclear regions in blue, the brightness of this hematoxylin-blue differs in both images.

Figure 2B:
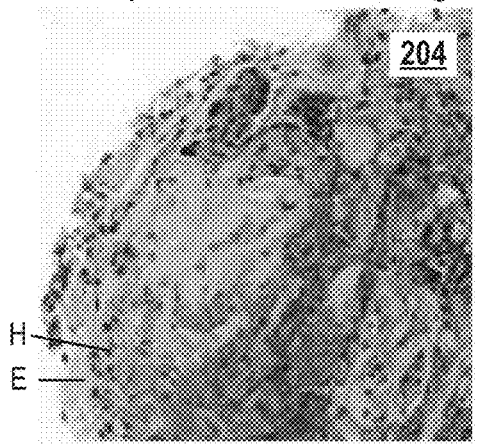
Figure 2B:
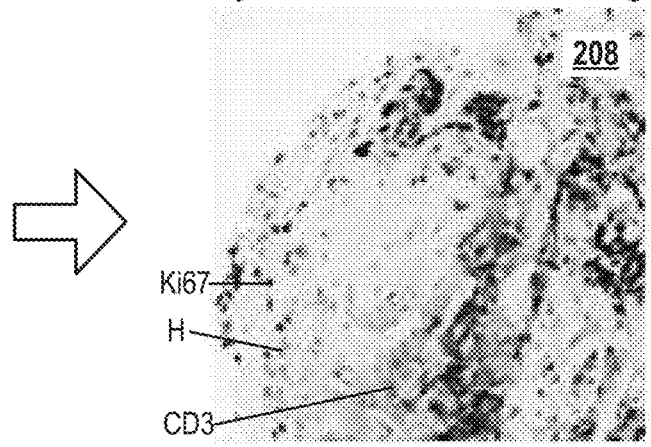

FIG. 2B depicts a further acquired input image 204 that depicts a further human liver tissue sample having been stained with H&E stain and depicts a corresponding output image 208 having been generated from the acquired image by the MLL in an image transformation operation. It should be noted that both virtual staining images 206, 208 where provided to a pathologist who was not able to recognize that the output images 206, 208 were not acquired by an image acquisition system but rather were computationally generated.

Figure 2C:
Figure 2C:
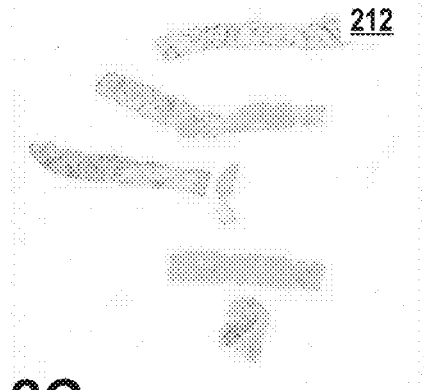

FIG. 2C depicts an acquired input image 210 that depicts multiple human liver tissue samples having been stained with H&E stain and depicts a corresponding output image 212 having been generated from the acquired image 210 by the MLL in an image transformation operation. The output image looks like ("simulates") a plurality of human liver tissue samples having been stained with H, with a FAP-specific stain (purple) and with a further stain (yellow) bound to a panCK antibody, wherein a panCK antibody is an antibody adapted to selectively bind to human epidermal cytokeratins. As can be derived from figure 212, the MLL is able to predict, based on image features in the input image 210 not visible to the human eye, that some of the tissue samples depicted in the acquired image 210 show a strong expression of cytokeratins while others do not. Those tissue samples and tissue regions having a high cytokeratin expression are virtually stained in a particular color used during the training of the MLL for staining the biomarker of interest, e.g. yellow color, as depicted in image 212.

Figure 2D:
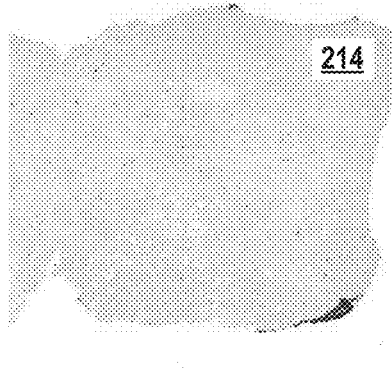
Figure 2D:
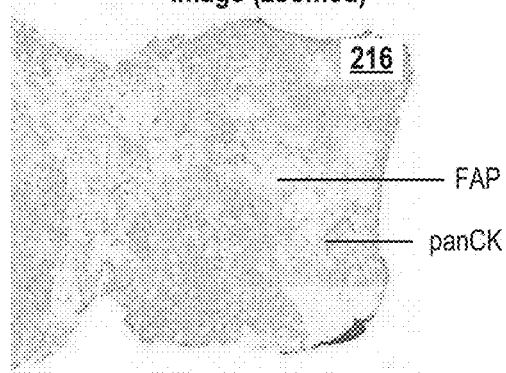

FIG. 2D depicts an acquired input image 218 that is a (zoomed) sub-region of the input image 210 of FIG. 2C and depicts an output image 216 that is a (zoomed) sub-region of the output image 212 of FIG. 2C.

Figure 2E:
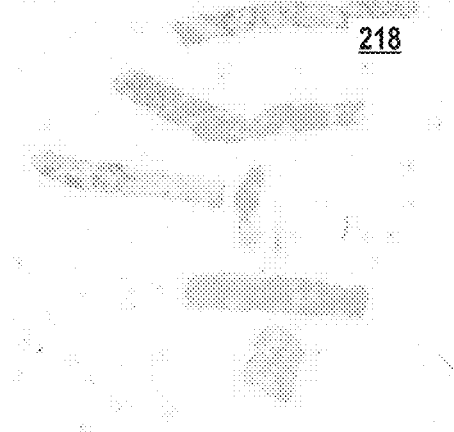
Figure 2E:
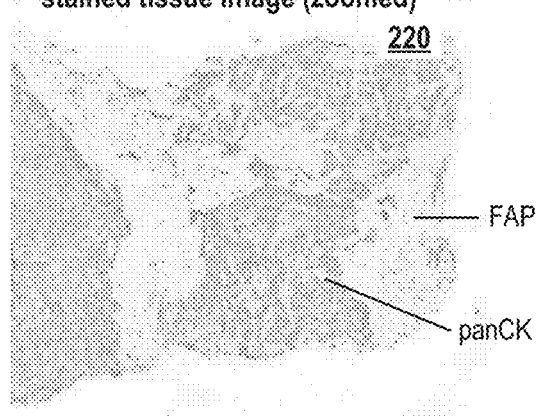

FIG. 2E depicts an acquired bright field image 218 of a tissue slice that was really stained with hematoxylin (H) and with a FAP-specific purple stain and with a yellow stain bound to a panCK antibody. This tissue slice was derived from the same tissue sample from which the H&E image 210 was acquired. Image 220 is a (zoomed) sub-region of the acquired image 218. Thus, a comparison of acquired image 218 with the virtually stained image 212 and a comparison of the zoomed acquired image 220 with the zoomed virtually stained image 216 reveals that the virtually stained images is indistinguishable from an image of a tissue sample that was really stained with the respective stains.

The FAP protein was stained with a FAP-specific antibody labeled with the DISCOVERY Purple Kit of Ventana. The cytokeratins were stained with a panCK antibody labeled with the DISCOVERY Yellow Kit of Ventana. Other stains can likewise be used for staining the biomarkers of interest for generating training images.

Figure 2F:
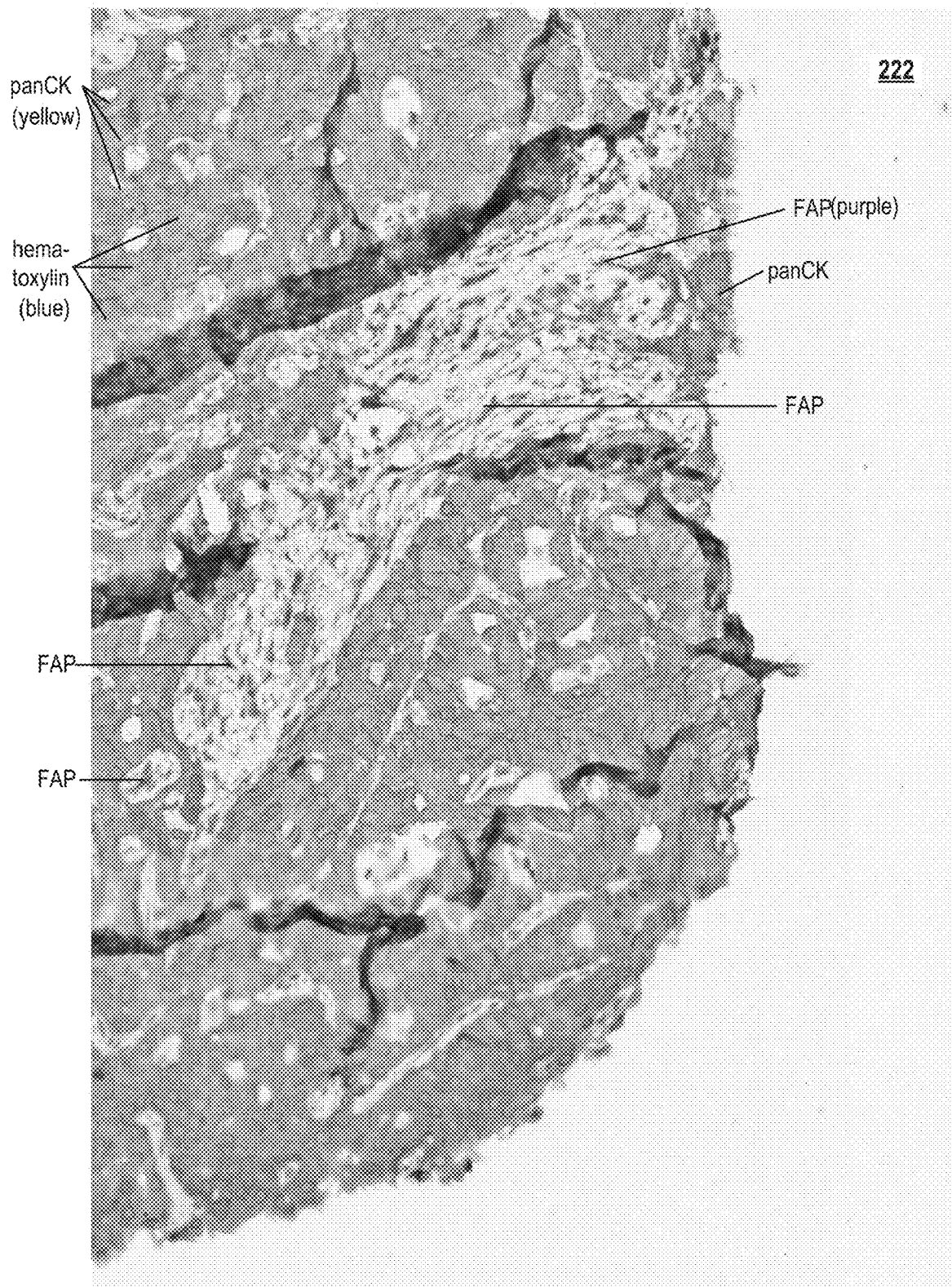

FIG. 2F depicts an acquired bright field microscope input image 222 that depicts a human liver tissue sample having been stained with hematoxylin and with a yellow stain coupled to a pan-CK antibody and with a purple stain bound to a FAP-specific antibody. The FAP regions appear as purple lines, cell nuclei stained with hematoxylin appear blue, and the panCK stained regions appear as yellowish environment of the stroma cells of the tissue.

Figure 2G:
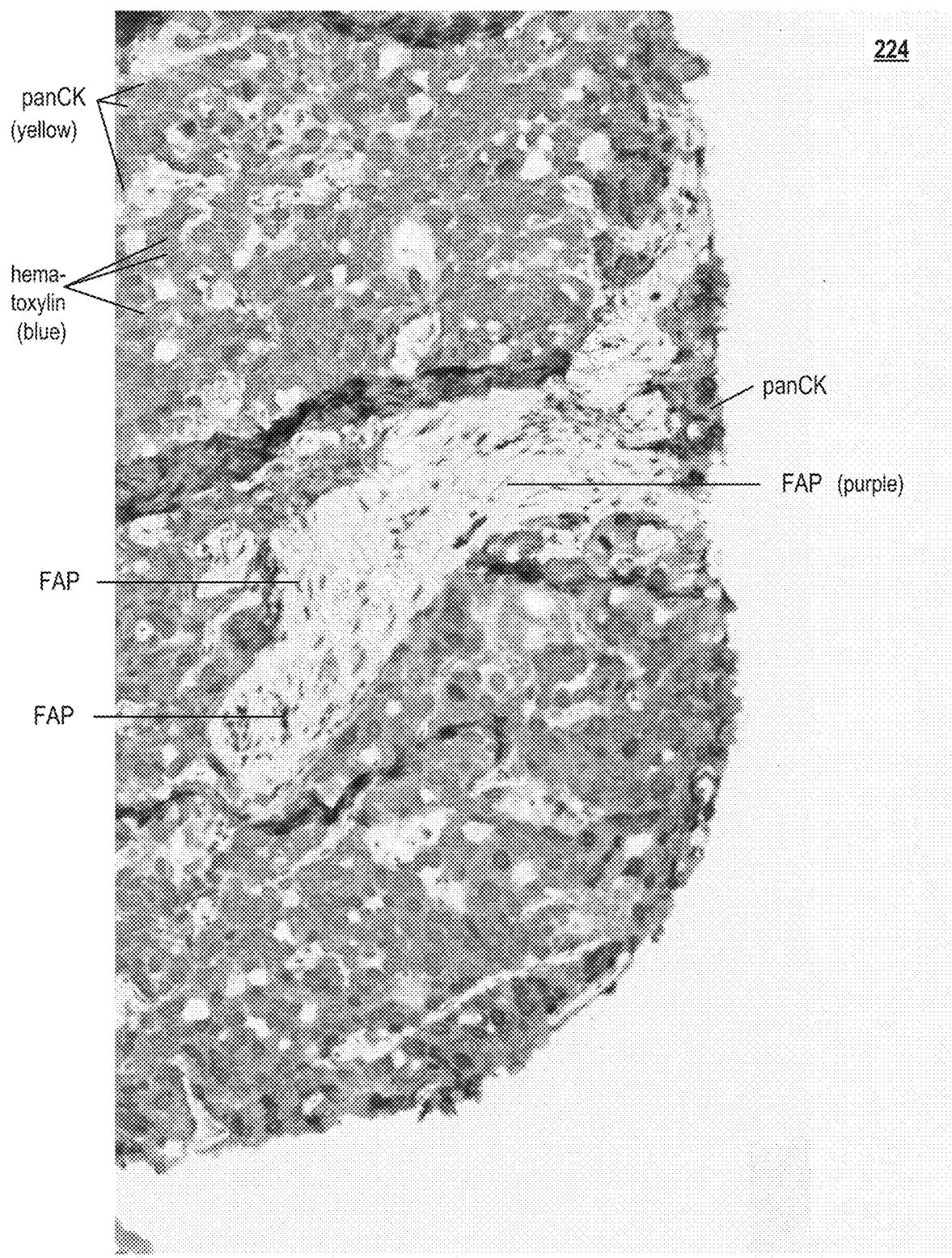

FIG. 2G depicts a virtually stained image 224 that was generated by an MLL from an acquired image, whereby said acquired image depicts a human liver sample having been stained with Ki67 specific brown stain comprising DAB and with a CD8 specific red stain comprising fastRed (not shown). The virtually stained image 244 looks highly similar to a bright field image of a tissue sample having really been stained with hematoxylin and with a FAP-specific purple stain and with a yellow stain bound to a panCK antibody.

FIG. 3 depicts a block diagram of an image analysis system 300 according to an embodiment of the invention.

The image analysis system 300 comprises one or more processors 302 and a volatile or non-volatile storage medium 306. For example, the storage medium 306 can be a hard disk drive, e.g. an electromagnetic or flash drive. It can be a magnetic, semi-conductor based or optic data storage. The storage medium can be a volatile medium, e.g. the main memory, which only temporarily comprises data.

The storage medium comprises one or more acquired images 202, 204, 316. An acquired image is an image having been acquired by an image acquisition system. An acquired image may have been computationally modified, e.g. for improving the contrast or for removing some artifacts, but is not completely generated/stimulated by a computer but is rather generated by an image acquisition operation. Thus, an acquired image is an "empirical image" while the output image 318 generated by an image transformation process is a basically computation-based ("virtual") image.

In some example embodiments, the image analysis system is coupled to an image acquisition system 320, e.g. a brightfield microscope, a fluorescent microscope, or an X-ray microscope and can receive the acquired image directly from the image acquisition system. Alternatively, the acquired image can be received via a network or can be read from the storage medium 306 or from another storage medium, e.g. a network drive or a cloud storage. As was explained already for embodiments described above, the acquired image can be one of a plurality of different image types, e.g. an auto-fluorescent image of a tissue sample, or a tissue sample image generated by an X-ray microscope or by a brightfield microscope. The tissue sample depicted in the acquired image can be unstained, or can be stained with one or more non-biomarker specific stains or can be stained with one or more first biomarker specific stains. In any case, the tissue sample depicted in the received acquired image has not been stained with biomarker specific stains adapted to selectively bind to one or more second biomarkers of interest.

A program logic 310, e.g. a piece of software written in Java, Python, C #, or any other suitable programming language, is adapted to receive the acquired image 316 and provided as input to the MLL 308 having been instantiated on the image analysis system 300. The MLL has been trained to identify tissue regions predicted to comprise a second biomarker based on training images whose type is identical to the type of the received acquired image. In some embodiments, the storage medium 306 of the image analysis system comprises multiple different MLLs 308 respectively having been trained on training images of different types (e.g. autofluorescence, brightfield, X-ray microscope, various combinations of non-biomarker-specific stains and/or first biomarker-specific stains). Thus, acquired images of many different types can be used as a basis for image transformation and for generating virtually stained output images.

The program logic 310 triggers the MLL to automatically transform the acquired image 316 having been provided as input into an output image 206, 208, 318. The output image can be, in particular, a virtual staining image 206, 208 as depicted for example in FIG. 2. The output image highlights tissue regions predicted to comprise the second biomarker.

In some embodiments, multiple different first stains are used to specifically stain a respective number of first biomarkers and labeled them with a respective distinguishable fluorescent label. The color differences of the different first stains provide a way to identify the positions of specific first biomarkers. A plurality of protocols for preparing conjugates of fluorophores and antibodies adapted to selectively bind to specific proteins are extensively described in the literature and do not require exemplification here. More than 120000 commercially available antibodies exist which used for research and for diagnosis of various diseases, including, for example, anti-estrogen receptor antibody (breast cancer), anti-progesterone receptor antibody (breast cancer), anti-p53 antibody (multiple cancers), anti-Her-2/neu antibody (multiple cancers), anti-EGFR antibody (epidermal growth factor, multiple cancers), anti-cathepsin D antibody (breast and other cancers), anti-Bcl-2 antibody (apoptotic cells), anti-E-cadherin antibody, and many others.

Fluorophores that may be conjugated to a primary antibody such that a first or a second stain is provided include but are not limited to Fluorescein, Rhodamine, Texas Red, Cy2, Cy3, Cy5, VECTOR Red, ELF™ (Enzyme-Labeled Fluorescence), Cy0, Cy0.5, Cy1, Cy1.5, Cy3, Cy3.5, Cy5, Cy7, Fluor X, Calcein, Calcein-AM, CRYPTOFLUOR™'S, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-[6-(7-nitrobenz-2-oxa-1,3-diazol-4-yl)-amino]caproyl] (NBD), BODIPY™, boron dipyrromethene difluoride, Oregon Green, MITOTRACKER™ Red, DiOC7 (3), DiIC18, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, NADH, NADPH, FAD, Infra-Red (IR) Dyes, Cyclic GDP-Ribose (cGDPR), Calcofluor White, Lissamine, Umbelliferone, Tyrosine and Tryptophan. A wide variety of other fluorescent probes are available from and/or extensively described in the Handbook of Fluorescent Probes and Research Products 8th Ed. (2001), available from Molecular Probes, Eugene, Oreg., as well as many other manufacturers.

For example, a slide-mounted tissue sample is stained with one of the dilution series of the primary antibody utilizing common immunohistochemistry techniques described above. The resulting stained specimens are each imaged using an image acquisition system 320 for viewing the detectable signal and acquiring an acquired image 316, such as a digital image of the staining. The images thus obtained are then used by the method of the invention for generating respective output images 318 respectively highlighting a second biomarker of interest for which no biomarker specific stain was applied on the sample before. The acquired images and the respective output images can be displayed to a user on a display screen 304.

The image acquisition system 320 can be, for example, any optical or non-optical image acquisition system such as, for example, upright or inverted optical microscopes, scanning confocal microscopes, cameras, scanning or tunneling electron microscopes, scanning probe microscopes, and imaging infrared detectors etc.

In one embodiment, the imaging device is a microscope system that includes one or more illumination sources 328 configured to illuminate a tissue sample 324 placed on a carrier slide 326. The system 320 may further comprise optics configured to produce a magnified image of the illuminated target sample, and a detector 322, such as a digital camera, configured to capture a digital image of the magnified image. A tissue sample or tissue microarray can be placed by a user on a sample stage. The user adjusts the sample stage so that a first region of interest is at the center of the field of view and focused on by the CCD camera. The objective lens should be adjusted to the appropriate resolution. Then the image acquisition system acquires images of the entire tissue sample or microarray or acquires images of parts (tiles) of the samples. Using commercially available software, the computer then can generate a composite image of the entire tissue sample or microarray.

The MLL 308 can be implemented, for example, as a cyclic GAN comprising two neural networks 312, 314 contesting with each other in a zero-sum game framework. During training, the first network 312 "learns" how to transform an acquired training image into an output training image highlighting tissue regions comprising one or more second biomarkers of interest such that the second network 314 cannot determine if the output image is an acquired training image of the second category, i.e., an acquired image of a real training tissue sample having been stained with one or more second stains selectively staining the one or more second biomarkers of interest, or is a virtual staining image having been computationally generated by the first neuronal network 312. Thereby, the second network 314 "learns" how to distinguish the virtual staining images generated by the first neuronal network 312 from "real", acquired images of the second category. In some embodiments, the first neuronal network learns, during the training phase, a mapping G:X→Y such that the distribution of virtual staining images generated by the mapping (which can also be referred to as "image transformation") from G(X) is indistinguishable from the distribution Y using an adversarial loss. A training image X of the first category may also be referred to as a "first training image" and the image Y of the second category may also be referred to as "second training image". In addition, the first neuronal network learns an inverse mapping (that may also be referred to as reverse image transformation) F:Y→X and evaluates the amount of cycle consistency loss in order to modify the transformation G and the reverse transformation F such that the cycle consistency loss is minimized or reduced. The cycle consistency is the requirement that $F(G(X)) \approx X$ (and vice versa). During the training, the MLL, in particular the first neural network 312, learns a mapping G:X→Y such that the output $\hat{y}=G(x)$, $x \in X$, is indistinguishable from images $y \in Y$ by an adversary trained to classify $\hat{y}$ apart from y. Thus, the training of the MLL according to embodiments of the invention comprises exploiting the property that translation should be "cycle consistent" and employs the learning effect of two, complementary neural networks 312, 314.

LIST OF REFERENCE NUMERALS 102-108 steps
202 acquired image
206 output image
204 acquired image
208 virtual staining image
210 acquired H&E stained image
212 virtually stained image (H&E & FAP & panCK)
214 acquired H&E stained image—zoomed
216 virtually stained image (H&E & FAP & panCK)—zoomed
218 acquired image of a H&E & FAP & panCK stained sample
220 zoomed sub-region of image 218
222 acquired image of a H&E & FAP & panCK stained sample
224 virtually stained image of a H&E & FAP & panCK stained sample computed from an acquired H&E & Ki67 & CD8 stained image
300 image analysis system
302 processors
304 display
306 storage medium
308 machine learning logic
310 program logic
312 first neural network
314 second neural network
316 acquired image
318 output image
320 image acquisition system
322 camera
324 tissue sample
326 slides
328 light sources

The invention claimed is:

1. A method of identifying a biomarker in a tissue sample comprising:
receiving, by an image analysis system, an acquired image, the acquired image having been acquired by an image acquisition system, the acquired image being:
a digital image of the tissue sample whose pixel intensity values correlate with the strength of an autofluorescence signal of the tissue sample;
providing a trained machine learning logic (MLL), the MLL having been trained to identify tissue regions predicted to comprise a first biomarker;
inputting the received acquired image into the MLL; and
automatically transforming, by the MLL, the acquired image into an output image, the output image highlighting tissue regions predicted to comprise the first biomarker.

2. The method of claim 1, wherein the output image is a virtual staining image, and the automatically transforming comprises:
setting the pixel intensity values of the image regions of the virtual staining image predicted to comprise the first biomarker such that they optically simulate the presence of a first biomarker-specific stain based on the strength of the autofluorescence signal of the tissue sample of the digital image, the first biomarker-specific stain being adapted to selectively stain the first biomarker.

3. The method of claim 1, wherein the first biomarker is a biomarker known to be selectively contained in one of a plurality of known immune cell sub-types, the first biomarker being one of: CD4, CD8, CD3, FAP, or Foxp3.

4. The method of claim 1, further comprising:
acquiring, by an image acquisition system, the acquired image, the image acquisition system being a fluorescence microscope.

5. The method of claim 1, further comprising generating the trained MLL, the generation comprising:
acquiring, by an image acquisition system, a plurality of first training images, each first training image depicting a respective training tissue sample and being:
a digital image of a training tissue sample, the pixel intensity values of said digital image correlating with and being indicative of the strength of an autofluorescence signal of the training tissue sample;
staining the training tissue samples with a first biomarker-specific stain, the first biomarker-specific stain being adapted to selectively stain the first biomarker in the training tissue samples;
acquiring, by the image acquisition system, a plurality of second training images, each second training image depicting a respective one of the training tissue samples having been stained with the first biomarker-specific stain; and
inputting the first and second training images pair wise into an untrained version of the MLL, each pair of training images depicting the same training tissue sample and being pixel-wise aligned to each other, and training the MLL such that the MLL learns to identify regions in the second training images depicting tissue regions in the training tissue samples which are predicted to comprise the first biomarker using intensity information contained in the first training image which depicts the same training tissue sample.

6. The method of claim 5, wherein the training of the MLL further comprises training the MLL to learn an image transformation routine, the image transformation routine being adapted to transform each of the first training images into a virtual staining image that is identical or similar to the one of the second training images having been obtained for the same training tissue sample.

7. The method of claim 1, wherein the MLL is a neural network, and the neural network is one of at least fully convolutional network or a network having conditional generative adversarial network (GAN) architecture.

8. The method of claim 1, further comprising generating the trained MLL, the generation comprising:
acquiring, by an image acquisition system, a plurality of first training images, each first training image depicting a respective training tissue sample and being:
a digital image of a training tissue sample, the pixel intensity values of said digital image correlating with and being indicative of the strength of an autofluorescence signal of the training tissue sample;
staining unstained or de-stained versions of the training tissue samples used for acquiring the first training images or staining unstained training tissue samples with the first biomarker-specific stain, the first biomarker-specific stain being adapted to selectively stain the first biomarker in the training tissue samples;
acquiring, by the image acquisition system, a plurality of second training images, each second training image depicting a respective one of the training tissue samples having been stained with the first biomarker-specific stain; and
inputting the first and second training images into an untrained version of the MLL, wherein the first and second training images depicting the same training tissue sample, if any, are neither assigned nor aligned with each other, and training the MLL such that the MLL learns to identify regions in the second training images depicting tissue regions in the training tissue samples which are predicted to comprise the first biomarker using intensity information contained in the first training image which depicts the same training tissue sample.

9. The method of claim 8, wherein the training tissue samples depicted in the first training images are derived from different tissue blocks or different patients than the further training tissue samples depicted in the second training images.

10. The method of claim 1, wherein the MLL is a generative adversarial network, in particular a cyclic generative adversarial network or a network having DISCO-GAN architecture.

11. The method claim 1, wherein the training of the MLL further comprises training the MLL to learn an image transformation routine, the image transformation routine being adapted to transform each of the first training images into a virtual staining image that is identical or similar to one of plurality of second training images having been obtained for the same training tissue sample.

12. An image analysis system comprising:
one or more processors;
a volatile or non-volatile storage medium, the storage medium comprising an acquired image, the acquired image having been acquired by an image acquisition system, the acquired image being,
a digital image of a tissue sample whose pixel intensity values correlate with the strength of an autofluorescence signal of the tissue sample, the storage medium further comprising a trained machine learning logic (MLL), the MLL having been trained to identify tissue regions predicted to comprise a first biomarker; and
a program logic executable by the one or more processors and configured to input the received acquired image into the MLL,
the MLL being configured to automatically transform the acquired image into an output image, the output image highlighting tissue regions predicted to comprise the first biomarker, and
the output image is a virtual staining image generated based on the strength of the autofluorescence signal of the tissue sample of the digital image.

13. An image-to-image translation method comprising:
receiving, by an image analysis system, a digital pathology image of a first desired category; and
automatically transforming, by a machine learning logic (MLL) being a trained generative adversarial network (GAN) network, the GAN network being a cyclic GAN or a network having conditional GAN architecture or a network having a discover cross-domain relations (DISCO)-GAN architecture, the digital pathology image of the first desired category into a digital pathology image of a second desired category;
wherein the digital pathology image of the first desired category is an acquired image highlighting first regions of a tissue sample, the first regions being auto-fluorescent regions; and
wherein the digital pathology image of the second desired category is a virtual staining image, the virtual staining image highlighting second regions of the tissue sample, the second regions being regions of the tissue sample predicted by to comprise a first biomarker, the virtual staining image generated based on the strength of the auto-fluorescent regions of the tissue sample of the digital pathology image of the first desired category.

* * * * *